United States Patent [19]

Rittershaus et al.

[11] Patent Number: 5,766,947

[45] Date of Patent: Jun. 16, 1998

[54] MONOCLONAL ANTIBODIES REACTIVE WITH AN EPITOPE OF A Vβ3.1 VARIABLE REGION OF A T CELL RECEPTOR

[75] Inventors: Charles W. Rittershaus, Malden; Patrick C. Kung, Lexington; Nancy Jones, Wayland, all of Mass.

[73] Assignee: Astra AB, Sodertalje, Sweden

[21] Appl. No.: 938,906

[22] Filed: Aug. 31, 1992

Related U.S. Application Data

[63] Continuation-in-part of Ser. No. 449,692, Dec. 11, 1989, Pat. No. 5,223,426, which is a continuation-in-part of Ser. No. 343,189, Apr. 25, 1989, abandoned, which is a continuation-in-part of Ser. No. 284,511, Dec. 15, 1988, abandoned, which is a continuation-in-part of Ser. No. 284,141, Dec. 14, 1988, abandoned.

[51] Int. Cl.$^6$ .................. C07K 16/28; C07K 16/46; C12N 5/12; C12N 5/20

[52] U.S. Cl. .................. 435/334; 435/343.2; 435/346; 530/388.22; 530/388.75; 530/809; 530/387.1; 530/387.9; 530/386.4; 530/386.15; 424/142.1; 424/144.1; 514/825

[58] Field of Search .................. 424/85.8, 142.1, 424/144.1; 435/240.27, 334, 343.2, 346; 530/387.1, 387.9, 388.1, 388.15, 388.22, 388.75, 809; 514/825

[56] References Cited

U.S. PATENT DOCUMENTS

| | | |
|---|---|---|
| 4,367,221 | 1/1983 | Kasper . |
| 4,550,086 | 10/1985 | Reinherz et al. . |
| 4,845,026 | 7/1989 | Kung et al. . |
| 4,886,743 | 12/1989 | Hood et al. . |
| 4,923,799 | 5/1990 | Mak et al. . |
| 5,179,018 | 1/1993 | Bogard et al. . |
| 5,223,426 | 6/1993 | Skibbens et al. . |

FOREIGN PATENT DOCUMENTS

| | | |
|---|---|---|
| 0180171 A2 | 10/1985 | European Pat. Off. . |
| 0180878 A2 | 10/1985 | European Pat. Off. . |
| 0200350 A2 | 3/1986 | European Pat. Off. . |
| 0289252 A2 | 11/1988 | European Pat. Off. . |
| 0340109 A2 | 4/1989 | European Pat. Off. . |
| 0250333 A1 | 10/1987 | German Dem. Rep. . |
| 61-254529 | 11/1986 | Japan . |
| 63-030500 | 2/1988 | Japan . |
| 2197323 | 5/1988 | United Kingdom . |
| WO 84/02848 | 8/1984 | WIPO . |
| WO 88/00209 | 1/1988 | WIPO . |
| WO 89/02899 | 4/1989 | WIPO . |
| WO 89/05309 | 6/1989 | WIPO . |
| WO 92/02629 | 2/1992 | WIPO . |
| WO 92/12996 | 8/1992 | WIPO . |

OTHER PUBLICATIONS

Gibbs et al. Scientific American 101–103 Jul. 1993.

Barsoum et al. Mol. Immunol. 22(4):361–7 1985 (see Abstract).

Liu et al. PNAS 84:3439–43 May 1987.

Wang et al. J. Parenteral Science and Technology 42(25):51–59 1988.

Immunotech International, 1992, "Catalog for Immunology".

Williams, et al., J. Clin. Invest. 90:326–333 (1992) "Restricted Heterogeneity of T Cell Receptor Transcripts in Rheumatoid Synovium".

Uematsu, et al., Proc. Natl. Acad. Sci. USA 88:8534–8538 (1991) "The T–Cell–Receptor Repertoire in the Synovial Fluid of a Patient with Rheumatoid Arthritis is Polyclonal".

Howell, et al., Proc. Natl. Acad. Sci. USA 88:10921–10925 (1991), "Limited T–Cell Receptor β–chain Heterogeneity Among Interleukin 2 Receptor–Positive Synovial T Cells Suggests a Role for Superantigen in Rheumatoid Arthritis".

Paliard, et al., Science 253:325–329 (1991), "Evidence for the Effects of a Superantigen in Rheumatoid Arthritis".

Axberg et al., Journal of Clinical Immunology 11:1–12 (1991), "Characterization of T–Cell Subsets and T–Cell Receptor Subgroups in Pigtailed Macaques Using Two–and Three–Color Flow Cytometry".

Gascoigne, J. Biol. Chem. 265:9296–9301 (1990), "Transport and Secretion of Truncated Cell Receptor β–Chain Occurs in the Absence of Association with CD3".

Posnett, et al., J. Clin. Invest. 85:1770–1776 (1990), "T Cell Antigen Receptor V Gene Usage".

Concannon, et al., Proc. Natl. Acad. Sci. USA 83:6598–6602 (1986), "Diversity and Structure of Human T–Cell Receptor β–Chain Variable Region Genes".

Smith et al. J. Immunol. 3234–38 1990.

Gillies et al. Hum. Antibod. Hybridomas 1(1):47–54 1990.

Lazar et al. Mol. Cell. Biology 8(3):1247–1252 1988.

Burgess et al. J. Cell Biology 111:2129–37 1990.

Maecker and Levy (1989), J. Immunol. 142:1395–1404.

Posnett et al. (1986), Proc. Nat'l Acad. Sci. USA 83: 7888–7892.

Boylston et al. (1986), J. Immunol. 137: 741–744.

(List continued on next page.)

*Primary Examiner*—Anthony C. Caputa
*Attorney, Agent, or Firm*—Thomas R. Berka, PhD.; Leon R. Yankwich

[57] ABSTRACT

The invention is directed to monoclonal antibodies reactive with a member of the Vβ3 family variable region of the beta chain of the TCR. More particularly, the invention provides for detection of the Vβ3.1 subfamily. In a specific embodiment the invention provides for detection of Vβ3.1, without cross-reacting with other Vβ3 family variable regions. In a specific embodiment, the monoclonal antibodies of the invention do not react with Vβ3.2. In particular, the invention provides monoclonal antibodies, termed 5E4 and 8F10, which react with the variable region of a member of the Vβ3 family. In various embodiments of the invention, these antibodies, or fragments or derivatives thereof, can be used to bind with a member of the Vβ3 family TCR variable region amino acid sequences, either as part of an intact TCR or peptide, or T cell-surface molecule, or a fragment thereof. The monoclonal antibodies are useful for diagnosis and therapy of autoimmune disease, in particular rheumatoid arthritis.

11 Claims, 9 Drawing Sheets

OTHER PUBLICATIONS

Bigler and Chiorazzi, (1987) in the Molecular Basis of B-Cell Differentiation and Function, Ferrerini and Pernis, eds., Plenum Press, pp. 123–130.
Bigler et al. (1985), J. Exp. Med. 161: 1450–1463.
Bigler et al. (1983), J. Exp. Med. 158: 1000–1005.
Fabbi et al. (1985), Eur. J. Immunol. 15: 821–827.
Spits et al. (1985), J. Immunol. 135: 1922–1928.
Samelson et al. (1983), Proc. Nat'l Acad. Sci. U.S.A. 80: 6972–6976.
Reinherz et al. (1984), Immunol. Rev. 81: 95–129.
Meuer et al. (1983), J. Exp. Med. 157: 705–719.
McIntyre and Allison (1983), Cell 34: 739–746.
Marchalonis (1987), Antigen–Specific T–Cell Receptors and Factors, vols. I and II, Marchalonis (Ed.), CRC Press, Boca Raton, Florida, Table of Contents and pp. 18–21.
Brenner et al. (1984), J. Exp. Med. 160: 541–551.
Tian et al. (1989) FASEB J., 3: A486 (and poster).
Borst et al. (1987), J. Immunol. 139: 1952–1959.
Brenner et al. (1987), J. Immunol. 138: 1502–1509.
Maecker et al. (1987), J. Immunol. Methods 98: 219–226.
Picker et al. (1987), Am. J. Pathol. 129: 434–440.
Ng et al. (1988), Am. J. Pathol. 132: 365–371.
Moller et al. (1988), J. Clin. Invest. 82: 1183–1191.
Tillinghast et al. (1986), Science 233: 879–883.
Waldmann et al. (1985), New Eng. J. Med. 313: 776–783.
Schluter et al. (1986), Proc. Nat'l Acad. Sci. U.S.A. 83: 1872–1876.
Kappler et al. (1989), Science 244: 811–813.
Brennan et al. (1988), J. Autoimmun. 1: 319–326.
Grossi et al. (1989), Proc. Nat'l. Acad. Sci. U.S.A. 86: 1619–1623.
Wu et al. (1988), J. Immunol. 141: 1476–1479.
Augustin et al. (1989), Nature 340: 239–241.
Ferrini et al. (1987), J. Exp. Med. 166: 277–282.
Brenner et al. (1986) Nature 322: 145–149.
Compana et al. (1989), J. Immunol. 142: 57–66.
Janson et al. (1989a), Cancer Immunol. Immunother. 28: 225–232.
Janson et al. (1989b), in Human Tumor Antigens and Specific Tumor Therapy, Alan R. Liss, Inc. pp. 277–286.
Wraith et al. (1989), Cell 57: 709–715.
Howell et al. (1989), Science 246: 668–670.
Ashwell et al. (1987), Science 237: 61–64.
Urban et al. (1988), Cell 54: 577–592.
Acha–Orbea et al. (1988), Cell 54: 263–273.
Vacchio and Hodes (1989), J. Exp. Med. 170: 1335–1346.
Webb and Sprent (1987), J. Exp. Med. 165: 584–589.
Janson et al. (1987), Scand. J. Immunol. 26: 237–246.
Behlke et al. (1987), J. Exp. Med. 165: 257–262.
Fowlkes et al. (1987) Nature 329: 251–254.
Payne et al. (1988) Proc. Nat'l Acad. Sci. U.S.A. 85: 7695–7698.
Staerz et al. (1985), J. Immunol. 134: 3994–4000.
Haskins et al. (1984), J. Exp. Med. 160: 452–471.
Chan and Takei (1986), J. Immunol. 136: 1346–1355.
Guy et al. (1989), Science 244: 1477–1480.

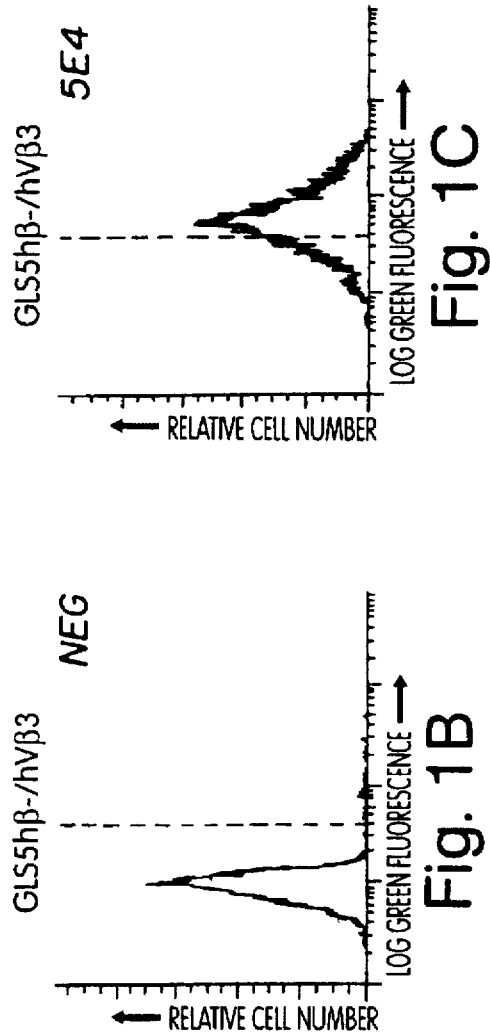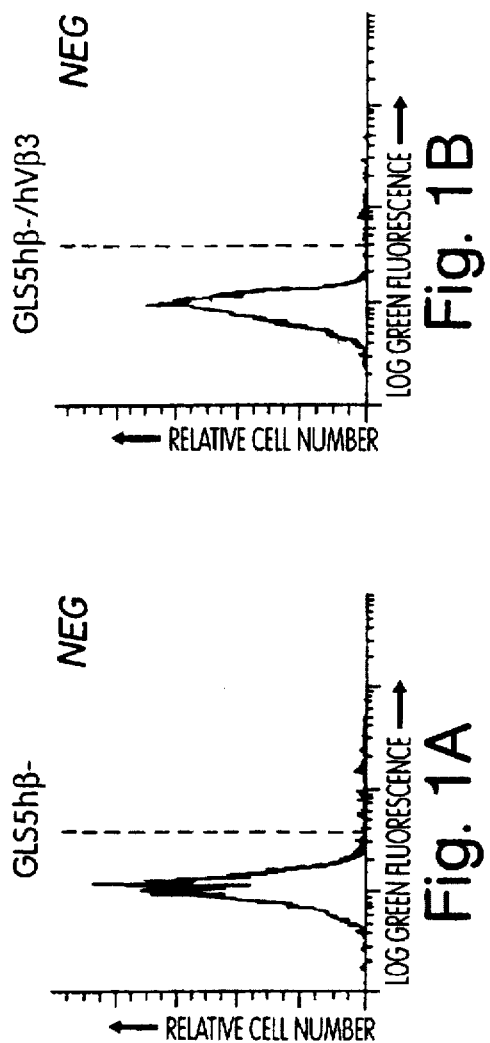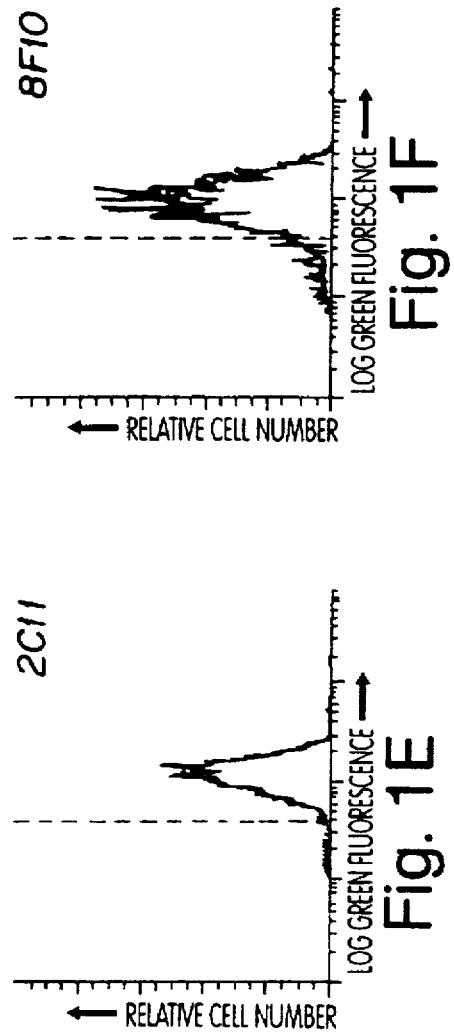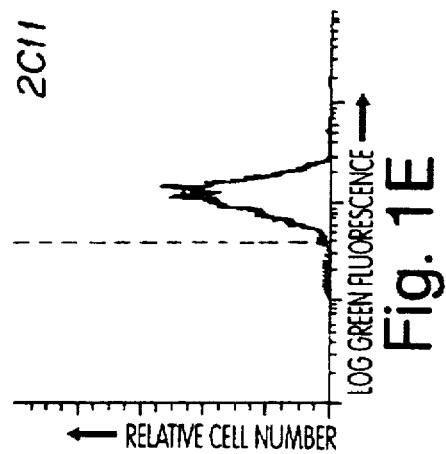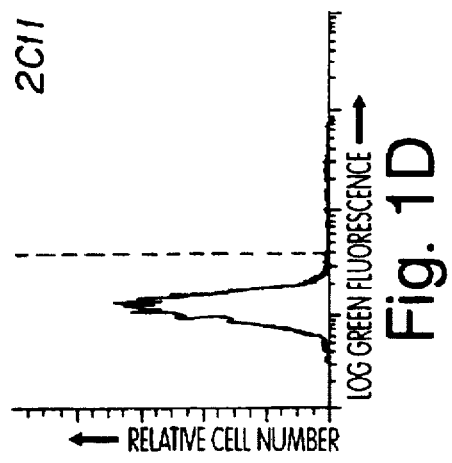

|  | ▼ V | N + D | J | C ▲ |
|---|---|---|---|---|
| PL4.4 Jβ2.5 | GCC AGC | AGT TCC AAA AAC AGG GGA TGG | GAG ACC CAG TAC TTC GGG CCA GGC ACG CGG CTC ACG GTC ACA | GAG |
| 5E4 Seqs. | | | | |
| #2 Jβ2.7 | GCC AGC | AGT CCA GGG GGA AG | C GAG CAG TAC TTC GGG CCG GGC ACC AGG CTC ACG GTC ACA | GAG |
| #11 Jβ2.7 | GCC AGC | AGT TTT CGG GTC GG | C GAG CAG TAC TTC GGG CCG GGC ACC AGG CTC ACG GTC ACA | GAG |
| #17 Jβ2.7 | GCC AGC | AGC CAC GCA CAG CGG GGG GAC AGG GAG GGG ATG C | C GAG CAG TAC TTC GGG CCG GGC ACC AGG CTC ACG GTC ACA | GAG |
| #10 Jβ2.7 | GCC AGC | AGC CAT GGG GGG CGG GGG GAC AGG CAG GGG CCT | C GAG CAG TAC TTC GGG CCG GGC ACC AGG CTC ACG GTC ACA | GAG |
| # 4 Jβ2.7 | GCC AGC | AGT TTA TTG ATC AGG GTA CGA GAA | CC TAC GAG CAG TAC TTC GGG CCG GGC ACC AGG CTC ACG GTC ACA | GAG |
| #16 Jβ2.6 | GCC AGC | AGT TTA AGG CCT CCT AGC GGG CCC G | CC TAC GAG GTC CTG ACT TTT GGG GCC GGC AGC AGG CTG ACC GTG CTG | GAG |
| # 9 Jβ2.2 | GCC AGC | AGT ACC CAT AGC GGG CCC G | GGG GCC GAG CTG TTT TTT GGA GAA GGC TCT AGG CTG ACC GTA CTG | GAG |
| # 8 Jβ1.5 | GCC AGC | AAA GAG GAC AGG GAG GGT TGA G | AC ACC CCC CAT TTT GGT GAT GGG ACT CGA CTC TCC ATC CTA | GAG |
| 8F10 Seqs. | | | | |
| #33 Jβ2.7 | GCC AGC | AGT TTT AGC GGA GGG G | CC TAC GAG CAG TAC TTC GGG CCG GGC ACC AGG CTC ACG GTC ACA | GAG |
| #21 Jβ2.7 | GCC AGC | GCT GTA AGG GAC AGG CAG TTT CCC G | CC TAC GAG CAG TAC TTC GGG CCG GGC ACC AGG CTC ACG GTC ACA | GAG |
| #27 Jβ2.7 | GCC AGC | AGT TTG CGG GAG TTG TCT | TAC GAG CAG TAC TTC GGG CCG GGC ACC AGG CTC ACG GTC ACA | GAG |
| #29 Jβ2.7 | GCC AGC | ACC TCC CGG GAC AA | C TCC TAC GAG CAG TAC TTC GGG CCG GGC ACC AGG CTC ACG GTC ACA | GAG |
| #24 Jβ2.1 | GCC AGC | GGA ACA GGG AGG | AAT GAG CCC CAG TTC TTC GGG CCA GGG ACA CGG CTC ACC GTG CTA | GAG |
| #23 Jβ1.5 | GCC AGC | AGT TTT AGA CAG GGC CCA T | AT CAG CCC CAT TTT GGT GAT GGG ACT CGA CTC TCC ATC CTA | GAG |

Fig. 4

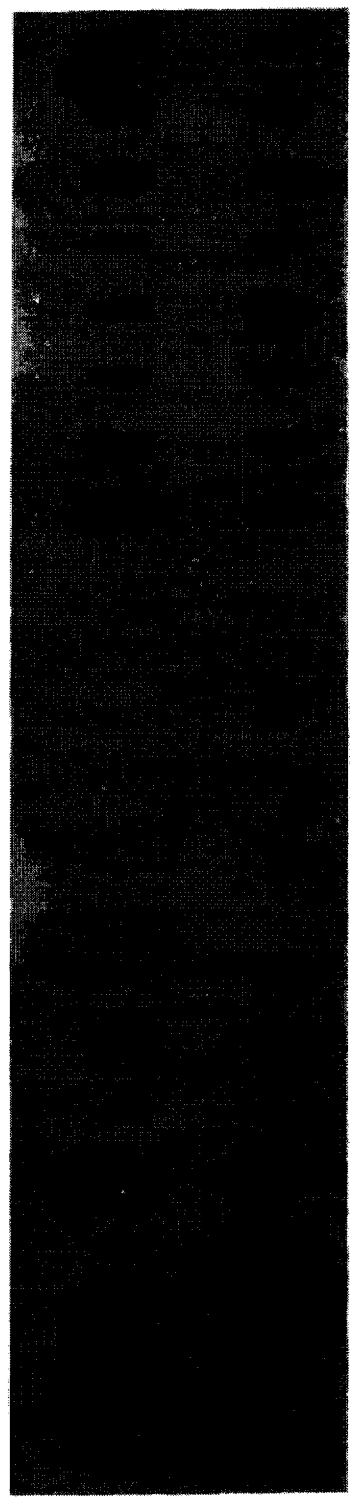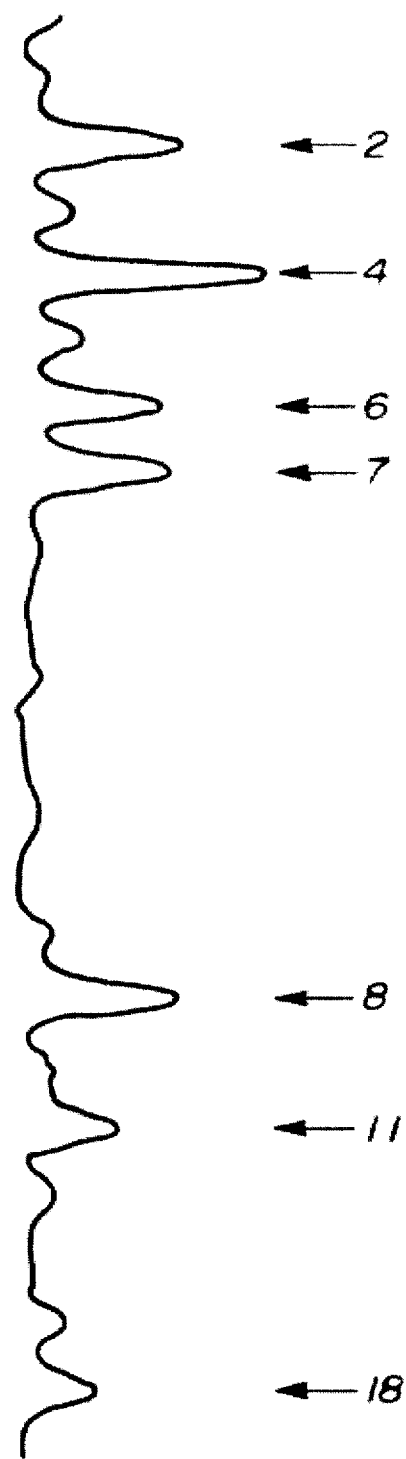
Fig. 6

MONOCLONAL ANTIBODIES REACTIVE WITH AN EPITOPE OF A Vβ3.1 VARIABLE REGION OF A T CELL RECEPTOR

This application is a continuation-in-part of U.S. patent application Ser. No. 07/449,692, filed Dec. 11, 1989 (now issued as U.S. Pat. No. 5,228,426), which was a continuation-in-part of U.S. Ser. No. 07/343,189, filed Apr. 25, 1989 (now abandoned), which was a continuation-in-part of U.S. Ser. No. 07/284,511, filed Dec. 15, 1988 (now abandoned), which was a continuation in part of U.S. Ser. No. 07/284,141, filed Dec. 14, 1988 (now abandoned). All of these applications are hereby incorporated by reference in their entirety.

1. FIELD OF THE INVENTION

The present invention in the field of immunology and medicine is directed to monoclonal antibodies which recognize defined regions of the T cell antigen receptor. These monoclonal antibodies are useful in the diagnosis and therapy of a variety of immune-related diseases and are useful tools for study of the immune system.

2. BACKGROUND OF THE INVENTION

2.1. THE T CELL ANTIGEN RECEPTOR

T lymphocytes interact with antigens through the T cell antigen receptor (TCR) complex. The TCR is a clone-specific heterodimer on T cells, which recognizes its target antigen in association with a major histocompatiblity antigen. The TCR has been shown to be noncovalently associated with the CD3 complex. TCR is highly polymorphic between T cells of different specificities. Approximately 90 percent of peripheral blood T cells express a TCR consisting of an α polypeptide and a β polypeptide. A small percentage of T cells have been shown to express a TCR consisting of a γ polypeptide and a δ polypeptide. (Regarding TCR molecules, see Davis and Bjorkman, 1988, Nature 334:395–402; Marrack and Kappler, 1986, Sci. Amer. 254:36; Meuer et al., 1984, Ann. Rev. Immunol. 2:23–50; Brenner et al., 1986, Nature 322:145–159; Krangel et al., 1987, Science 237:1051–1055; Hata et al., 1987, Science 238:678–682; Hochstenbach et al., 1988, J. Exp. Med. 168:761–776). The chains of the T cell antigen receptor of a T cell clone are each composed of a unique combination of domains designated variable (V), [diversity (D),] joining (J), and constant (C) (Siu et al., 1984, Cell 37:393; Yanagi et al., 1985, Proc. Natl. Acad. Sci. USA 82:3430). Hypervariable regions have been identified (Patten et al., 1984, Nature 312:40; Becker et al., 1985, Nature 317:430). In each T cell clone, the combination of V, D and J domains of both the alpha and the beta chains or of both the delta and gamma chains participates in antigen recognition in a manner which is uniquely characteristic of that T cell clone and defines a unique binding site, also known as the idiotype of the T cell clone. In contrast, the C domain does not participate in antigen binding.

2.2. T CELL ANTIGEN RECEPTOR GENES

TCR genes, like immunoglobulin genes, consist of regions which rearrange during T cell ontogeny (Chien et al., 1984, Nature 312:31–35; Hedrick et al., 1984, Nature 308:149–153; Yanagi et al., 1984, Nature 308:145–149). In genomic DNA, each TCR gene has V, J, and C regions; TCR β and δ polypeptides also have D regions. The V, D,J, and C regions are separated from one another by spacer regions in the genomic DNA. There are usually many variable region segments and somewhat fewer diversity, junctional, and constant region segments. As a lymphocyte matures, these various segments are spliced together to create a continuous gene sequence consisting of one V, (D), J, and C region.

TCR diversity, and thereby T cell specificity, is derived from several sources (Barth et al., 1985, Nature 316:517–523; Fink et al., 1986, Nature 321:219–225): a multiplicity of germline gene segments (Chien et al., 1984, Nature 309:322–326; Malissen et al., 1984, Cell 37:1101–1110; Gascoigne et al., 1984, Nature 310:387–391; Kavaler et al., 1984, Nature 310:421–423; Siu et al., 1984, Nature 311:344–349; Patten et al., 1984, Nature 312:40–46); combinatorial diversity through the assembly of different V, D, J, and C segments (Siu et al., 1984, Cell 37:393–401; Goverman et al., 1985, Cell 40:859–867); and junctional flexibility, N-region diversity and the use of either multiple D regions or any of the three translational reading frames for Dβ segments. TCR diversity does not appear to arise from the somatic hypermutation mechanism observed for immunoglobulins (Barth et al., supra). As a result of these mechanisms, TCRs are generated which differ in their amino-terminal, or N-terminal, domains (called variable, or V regions, constructed from combinations of V, D, and J gene segments) but are similar elsewhere, including their carboxy-terminal, or C-terminal domains (called constant regions). Accordingly, an almost limitless repertoire of TCR is established.

The β gene of the TCR appears to resemble most closely the immunoglobulin V gene in that it has three gene segments, Vβ, Dβ and Jβ which rearrange to form a contiguous β gene (Siu et al., 1984, Cell 37:393–401). The β locus has been well characterized in mice, where it spans 700–800 kilobases of DNA and is comprised of two nearly identical C regions tandemly arranged with one D element and a cluster of 5–6 J elements 5' to each (Kronenberg et al., 1986, Ann. Rev. Immunol. 3:537–560). Approximately twenty to thirty Vβ regions are located upstream (5') to the D, J, and C elements (Behlke et al., 1985, Science 229:566–570) although Vβ genes may also be located 3' to the murine Cβ genes (Malissen et al., 1986, Nature 319:28). Study of the structure and diversity of the human TCR β-chain variable region genes has led to the grouping of genes into distinct Vβ subfamilies (Tillinghast et al., 1986, Science 233:879–883; Concannon et al., 1986, Proc. Natl. Acad. Sci. USA 83:6598–6602; Borst et al., 1987, J. Immunol. 139:1952–1959).

The γ TCR gene was identified, first in mice (Saito et al., 1984, Nature 309:757–762; Kranz et al., 1985, Nature 313:762–755; Hayday et al., 1985, Cell 40:259–269) and then in humans (Lefranc et al., 1985, Nature 316:464–466; Murre et al., 1985, Nature 316:549–552). The human γTCR locus appears to consist of between five and ten variable, five joining, and two constant region genes (Dialynas et al., 1986, Proc. Natl. Acad. Sci. USA 83:2619).

The TCR α and δ locus are next to one another on human chromosome 14. TCR δ coding segments are located entirely within the α gene locus (Satyanarayana et al., 1988, Proc. Natl. Acad. Sci. USA 85:8166–8170; Chien et al., 1987, Nature 330:722–727; Elliot et al., 1988, Nature 331:627–631). It is estimated that there are a minimum of 45–50 Vα regions (Becker et al., Nature 317:430–434) whereas there are only approximately 10 Vδ regions (Chien et al., 1987, supra). In peripheral blood, two predominant Vδ genes appear to be expressed, namely, Vδ 1 and Vδ 2, identifiable by monoclonal antibodies, δ TCS1 and BB3, respectively. Nucleic acid sequences of TCR α genes have been reported (Sim et al., 1984, Nature 312:771–775; Yanagi et al., 1985, Proc. Natl. Acad. Sci. USA 82:3430–3434; Berkout et al., 1988, Nucl. Acids Res. 16:5208).

2.3. ANTIBODIES TO THE T CELL ANTIGEN RECEPTOR

Clonotypic antibodies react only with a particular clone of T cells. Acuto et al. produced clonotypic monoclonal antibodies against a human thymocyte cell line, and thereby identified the TCR in relatively undifferentiated T3$^+$ cells (1983, Cell 34:717–726). Meuer et al. showed that anti-TCR clonotypic monoclonal antibodies coupled to sepharose beads could induce production of interleukin-2 (1984, Proc. Natl. Acad. Sci. USA 81:1509–1513). Anti-TCR clonotypic antibody directed toward the CT8 cell line could only block cytotoxic effector cell function of that T cell line (Meuer et al., 1984, Ann. Rev. Immunol. 2:23–50). Antibodies which recognize TCR from many T cell lines recognize shared epitopes, or framework regions, of TCR proteins. Brenner et al. found that different cloned T cell lines shared antigenic determinants, none of which appeared to be accessible at the cell surface (1984, J. Exp. Med. 160:541–551). β-Framework-1 (β F1) monoclonal antibody reacts with a "hidden determinant" on the surface of viable T cells, and recognizes the TCR β polypeptide in Western blots (Brenner et al., 1987, J. Immunol. 138:1502–1509). Another antibody, WT31, originally thought to be a framework reagent is useful in cell binding, but is inefficient in immunoprecipitation studies (Spits et al., 1985, J. Immunol. 135:1922–1928). WT31 now appears to recognize a CD3 determinant or perhaps a combined αβ TCR: CD3 epitope.

2.4. RHEUMATOID ARTHRITIS

Rheumatoid arthritis (RA), a chronic, recurrent, inflammatory disease primarily involving joints, affects 1–3% of North Americans, with a female to male ratio of 3:1. Severe RA patients tend to exhibit extra-articular manifestations including vasculitis, muscle atrophy, subcutaneous nodules, lymphadenopathy, splenomegaly and leukopenia. Spontaneous remission may occur; other patients have brief episodes of acute arthritis with longer periods of low-grade activity; still others progress to severe deformity of joints. In some patients with rheumatoid arthritis, particularly those with long-standing disease, a constellation of symptoms called "Felty's syndrome" develops, in which the typical arthropathy is accompanied by splenomegaly and neutropenia. It is estimated that about 15% of RA patients (severe RA and Felty's syndrome) become completely incapacitated ("Primer on the Rheumatic Diseases", 8th edition, 1983, Rodman, G. P. & Schumacher, H. R., Eds., Zvaifler, N. J., Assoc. Ed., Arthritis Foundations, Atlanta, Ga.).

The antigenic stimulus initiating the immune response and consequent inflammation is unknown. Certain HLA types (DR4, Dw4, Dw14 and DR1) have an increased prevalence in RA, perhaps leading to a genetic susceptibility to an unidentified factor which initiates the disease process. The association with DR4 is highest for Felty's Disease and severe RA (Westedt, M. L., et al., Annals of Rheumatic Diseases, 1986, 45:534–538). Relationships between Epstein Barr virus and RA have been suggested. Synovial lymphocytes produce IgG that is recognized as foreign and stimulates a local immune response with production of anti-IgG-antibodies (rheumatoid factors). Immune complexes are formed by activation of the complement system which results in inflammation including activation of lysozyme and other enzymes. Helper T cell infiltration of the synovium and liberation of lymphokines such as IL6 lead to further accumulation of macrophages and slowly progressing joint destruction (erosions).

The approach to drug treatment in rheumatoid arthritis has been described as a pyramid ("Primer on the Rheumatic Diseases", supra). First line agents include aspirin and NSAIDS (non-steroidal anti-inflammatory drugs). When these agents fail, gold salts, penicillamine, methotrexate, or antimalarials, known as conventional second line drugs, are considered. Finally, steroids or cytotoxics are tried in patients with serious active disease that is refractory to first and second line treatment. Cyclosporine is now suggested to have a role in the treatment of patients whose disease is unresponsive to aspirin, NSAIDS, gold or penicillamine. However, the current experimental drugs to treat severe RA patients may prove too toxic even if they are effective.

Numerous efforts have been directed to developing safer and more efficacious immunotherapy to replace these toxic drugs. Severe RA patients who were treated with total lymphoid irradiation or thoracic duct drainage experienced significant improvement of disease symptoms. These procedures are not suitable for routine application. Due to these encouraging findings, however, and to the demonstration of the presence of T cells in the synovial infiltrate, it is possible to design new immunotherapies to specifically eliminate T cells. Most of these new experimental immunotherapies are targeted toward all or the bulk of T cells, and thus may produce significant side effects. A better approach for selective immunotherapy may be to eliminate only the subset of T cells that are involved in RA.

2.5. ROLE OF T CELLS IN RHEUMATOID ARTHRITIS

Evidence has accumulated supporting a role for T cells in the pathogenesis of rheumatoid arthritis (RA). The synovial tissue and surrounding synovial fluid of patients with rheumatoid arthritis (RA) are infiltrated with large numbers of cells. Activated and resting T cells can mediate tissue damage by a variety of mechanisms including the direct cytotoxicity of target cells expressing specific antigen in combination with the appropriate HLA restricting elements. The strong association of certain HLA products with RA has led researchers to implicate T cells in the autoimmune destruction of RA patient joints. In fact, HLA DR4, Dw4 and Dw14 gene products are among the major class II molecules that contribute significantly to disease susceptibility in RA patients (Nepom, B., et al., 1987, "Abstracts of Amer. Rheumatism Assoc.", p. S25; Todd, J. A., et al., 1988, Science 240:1003–1009), and they are capable of restricting antigen recognition of CD4+ T cells, primarily. Other autoimmune diseases also show a high correlation between disease susceptibility and HLA expression.

This genetic aspect of disease risk has encouraged the phenotypic analysis of the T cells found within diseased joints. Previously, comparisons of T cells from RA joints and RA peripheral blood (PB) demonstrated significant differences in CD4 or CD8 phenotype, therefore implying a selection of T cells involved in disease activity. Most studies agree that synovial tissue-infiltrated T cells were mostly CD4+ helper-inducer (4B4+) cells (Duke, O., et al., 1987, Arth. Rheum., 30, 849) while the PB usually contained a mixture of CD4+ and CD8+ cells including both helper-inducer cells and suppressor-inducer cells (2H4+) (Emery, P., et al., 1987, Arth. Rheum., 30, 849). In contrast, there is additional evidence that the CD4+ infiltrate may be predominantly suppressor-inducer cells (2H4+) (Mikasaka, N., et al., 1987, Amer. Rheum. Abstracts, p. S39).

3. SUMMARY OF THE INVENTION

The invention is directed to monoclonal antibodies reactive with a member of the Vβ3 family variable region of the beta chain of the TCR. More particularly, the invention provides for detection of the Vβ3.1 subfamily. In a specific embodiment the invention provides for detection of Vβ3.1, without cross-reacting with other Vβ3 family variable regions. In a specific embodiment, the monoclonal antibodies of the invention do not react with Vβ3.2. In particular, the invention provides monoclonal antibodies, termed 5E4 and 8F10, which react with the variable region of a member of the Vβ3 family. In various embodiments of the invention, these antibodies or fragments or derivatives thereof, can be used to bind with a member of the Vβ3 family TCR variable region amino acid sequences, either as part of an intact TCR or peptide, or T cell-surface molecule, or a fragment thereof.

In another specific embodiment, the invention is directed to monoclonal antibodies 5E4 and 8F10 as produced by hybridomas deposited with the ATCC and assigned accession numbers HB 11020 and HB 11021 respectively.

The present invention is also directed to a fragment of any of the above antibodies, preferably selected from the group consisting of a Fv fragment, a Fab fragment, a Fab' fragment and a F(ab')$_2$ fragment.

The invention is further directed to a hybridoma cell line producing any of the above mAbs.

The monoclonal antibodies of the invention have value in the diagnosis and therapy of conditions and diseases affecting the immune system.

In particular embodiments of the invention, rheumatoid arthritis may be diagnosed by detecting increased percentages of total T cells which express certain beta chain T cell receptor variable region genes in a patient sample. In specific embodiments of the invention, rheumatoid arthritis may be diagnosed by detecting increased percentages of total T cells that express Vβ3, Vβ9, or Vβ10 T cell receptor variable regions in a patient sample. The present invention provides for detection of T cells that express a member of the Vβ3 family, in particular Vβ3.1.

In yet another embodiment, the present invention provides a method for diagnosing the immune-related disease rheumatoid arthritis in a subject, wherein the disease is associated with a preferential usage of a Vβ3 family variable region of a T cell antigen receptor, the method comprising:

(a) contacting a biological sample from the subject with a monoclonal antibody, or a fragment or derivative thereof, reactive with an epitope of a member of the Vβ3 family variable region;

(b) detecting whether immunospecific binding has occurred and comparing the amount of antibody bound to an amount bound in a baseline sample in which an increase in the amount of antibody bound in the sample of the subject relative to the baseline sample is indicative of rheumatoid arthritis.

(c) For diagnosis of RA, preferably Vβ9, or Vβ10, or both, are detected in a sample from the subject. The amount of Vβ9 or Vβ10 expressed is compared with the amount expressed in the baseline sample. An increase in the amount in the sample of the subject relative to the baseline sample is indicative of rheumatoid arthritis in addition to Vβ3.

In the above method, the sample may be contacted in vitro or in vivo. In the in vitro method, the sample is preferably a body fluid, tissue or a histologic specimen.

A preferred method, as described above, is useful for diagnosing rheumatoid arthritis (RA) in a subject. In diagnosing RA, the sample is preferably selected from the group consisting of peripheral blood, synovial tissue, and synovial fluid.

In yet another embodiment, the invention provides a method of treating an immune-related disease or disorder in a subject, in particular rheumatoid arthritis, comprising administering to the subject a therapeutically effective amount of an antibody, or a fragment or derivative thereof, as described above.

Also provided herein is a pharmaceutical composition useful for diagnosing or treating an immune-related disease or disorder, in particular rheumatoid arthritis, comprising an antibody, fragment or derivative, as above, and a pharmaceutically acceptable excipient. Preferably the antibody is detectably labeled.

In further particular embodiments of the invention, rheumatoid arthritis may be treated by administering a therapeutically effective amount of a monoclonal antibody, or fragment or derivative thereof, which recognizes an epitope of the Vβ3 family variable region of the beta chain of a T cell antigen receptor, in particular an epitope unique to the Vβ3.1 variable region of the beta chain. According to specific embodiments, monoclonal antibodies which recognize epitopes of the Vβ3 family, in particular Vβ3.1, alone or in combination with antibodies which recognize epitopes of Vβ9 or Vβ10 variable regions of the T cell antigen receptor may be used to treat rheumatoid arthritis.

The present invention is also directed to a method of increasing the number of T cells expressing a member of the Vβ3 family, in particular a Vβ3.1, T cell antigen receptor variable region, comprising exposing T lymphocytes to an effective concentration of an antibody or fragment or derivative thereof reactive, as described above. The exposing may be performed in vivo or in vitro.

3.1. ABBREVIATIONS AND DEFINITIONS

As used herein, the following terms will have the meanings indicated:
C=constant
D=diversity
J=joining
V=variable
ELISA=enzyme linked immunosorbent assay
mAb=monoclonal antibody
PBL=peripheral blood lymphocytes
PMA=phorbol 12-myristate 13-acetate
PBS=phosphate buffered saline
SDS-PAGE=sodium dodecylsulfate polyacrylamide gel electrophoresis
TCR=T cell antigen receptor
RES=reticuloendothelial system
RA=rheumatoid arthritis
ST-line=RA synovial tissue-derived T cells
FS=Felty's Syndrome
EBV=Epstein-Barr virus
HLA=human leukocyte antigen
FCS=fetal calf serum anti-clonotypic antibody=an antibody that reacts solely with the T cell clone against which it was raised. Also referred to as an anti-idiotypic antibody.
anti-minor framework antibody=an antibody that reacts with a minor framework determinant present on a subset of T cells. Anti-minor framework antibodies recognize small percentages of PBLs, i.e., less than 20% in a normal subject. Anti-minor framework antibodies can be used to define closely related TCRs or TCR families.

anti-major framework antibody=an antibody that reacts with a major framework determinant present on a large population of T cells.

BRIEF DESCRIPTION OF THE DRAWINGS

FIGS. 1A–1B. A series of graphs showing flow cytometry cytometric analysis of the reactivity of murine mAbs 5E4 and 8F10 specific for human TCR Vβ3 epitopes with murine T cells transfected with human Vβ3. Transfectants (FIGS. 1B, 1C, 1E, & 1F) were stained with a mAb specific for murine T3 (2C11; FIG. 1E), 5E4 (FIG. 1C), or 8F10 (FIG. 1F) by indirect immunofluorescence. Binding of the two murine anti-Vβ3 mAbs was detected with a FITC-conjugated goat anti-mouse Ig reagent. Hamster mAb 2C11 binding was detected with a FITC-conjugated anti-hamster Ig reagent (FIG. 1B). Also shown is the control reactivity of the untransfected parental mutant line within the anti-transfer Ig reagent (FIG. 1A) and 2C11 (FIG. 1D).

FIGS. 3A-1, 3A-2, 3A-3, 3B-1, and 3B-2. Reactivity of 5E4 and 8F10 with human PBL. (FIGS. 3A-1, 3A-2, and 3A-3) Two color immunofluorescence analysis using anti-CD3 phycoerythrin and either negative control IgG1 mAb, 5E4 or 8F10 as indicated. Binding of the latter 3 mAb was detected using FITC-conjugateed goat anti-mouse IgG; (FIGS. 3B-1 and 3B-2) 5E4 and 8F10 expression on CD4+or CD8+ T Cells. Two-color immunofluorescence employed either phycoerythrin conjugated antibodies to CD4 or CD8 with 5E4 or 8F10. The percentage of 5E4- or 8F10-reactive T cells that were also CD4 or CD8 positive is shown.

FIG. 4. Shows the V-D-J junctional sequences of human T cells stimulated by 5E4 (5E4$^+$ cells) or by 8F10 (8F10$^+$ cells). The nucleotide sequences of the V-D-J junctional region of eight 5E4 reactive and six SF10 reactive T cells are shown in comparison to the analogous region from the Vβ3.1 clone PL4.4. The 5' end of the Jβ sequences are identified by comparison with germ line sequences.

FIGS. 5-1, 5-2, and 5-3. Reactivity of FITC conjugated 5E4 and 8F10 with cynomolgus macaque PBL. FIG. 5-1 is a graph of 2-color immunofluorescence analysis using a combination of anti-CD4 and anti-CD8 phycoerythrin and negative control mAb. FIG. 5-2 is a graph of 2-color immunofluorescence analysis using a combination of phycoerythrin conjugated anti-CD4 and anti-CD8 and 8F10 to stain cynomolgous macaque PBL. FIG. 5-3 uses 5E4 as in FIG. 5-2 in place of 8F10. 8F10 stains a subpopulation of macaque PBL consisting of 1.4%. 5E4 stains a subpopulation consisting of 1.46%.

FIG. 6. Analysis of Vβ gene usage in synovial tissue derived T cell line. Line ST-2, derived from the synovial membrane-infiltrating cells of a RA patient, was analyzed for TCR Vβ expression using the cDNA, PCR amplification, slot blot hybridization protocol. The left panel represents the autoradiograph obtained when the panel of Vβ genes was hybridized with the ST-2 amplified TCR specific CDNA probe. The right panel of the figure is the densitometry trace of the autoradiograph.

5. DETAILED DESCRIPTION OF THE INVENTION

Figure 2:
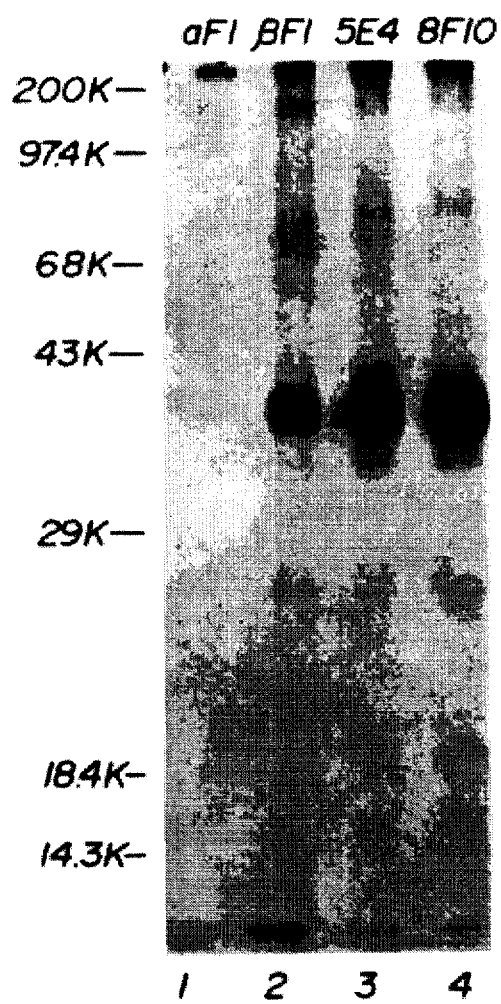
FIG. 2. Shows SDS-PAGE pattern of immunoprecipitation of TCR by 5E4 and 8F10 mAbs. Lane 1 shows an SDS-PAGE of immunoprecipitates of $^{125}$I-labeled murine cells expressing human Vβ3.1 cell surface proteins using αF1 as negative control (lane 1), βF1 as positive control (lane 2); mAb 5E4 (lane 3) and mAb 8F10 (lane 4). The positions of $^{14}$C-labeled molecular weight markers are denoted on the right.

In the following description, reference will be made to various methodologies known to those of skill in the art of immunology, cell biology, and molecular biology. Publications and other materials setting forth such known methodologies to which reference is made are incorporated herein by reference in their entireties as though set forth in full.

5.1. IMMUNE RELATED DISEASES

The term "immune-related disease" as used herein refers to a disease in which the immune system is involved in the pathogenesis of the disease, or in which appropriate stimulation of the immune system can result in protection from the disease. Relevant diseases include, but are not limited, to autoimmune diseases, neoplastic diseases, infectious diseases, hypersensitivity, transplantation, graft-versus-host disease, and degenerative nervous system diseases. Autoimmune diseases include, but are not limited to, arthritis, such as rheumatoid arthritis, type I diabetes, juvenile diabetes, multiple sclerosis, autoimmune thyroiditis (Hashimoto's thyroiditis), myasthenia gravis, systemic lupus erthematosis (SLE), Sjogren's syndrome, Grave's disease, Addison's disease, Goodpasture's syndrome, scleroderma, dermatomyositis, myxoedeman, polymyositis, pernicious anemia, inflammatory bowel disease including Crohn's disease and autoimmune atrophic gastritis, and autoimmune hemolytic anemia. Neoplastic diseases include, but are not limited to, lymphoproliferative diseases such as leukemias, lymphomas, Non-Hodgkin's lymphoma, and Hodgkin's lymphoma, and cancers such as cancer of the breast, colon, lung, liver, pancreas, etc. Infectious diseases include but are not limited to viral infections caused by viruses such as HIV, HSV, EBV, CMB, Influenza, Hepatitis A, B, or C; fungal infections such as those caused by the yeast genus Candida; parasitic infections such as those caused by schistosomes, filaria, nematodes, trichinosis or protozoa such as trypanosomes causing sleeping sickness, plasmodium causing malaria or leishmania causing leischmaniasis; and bacterial infections such as those caused by mycobacterium, corynebacterium, or staphylococcus. Hypersensitivity diseases include but are not limited to Type I hypersensitivities such as contact with allergens that lead to allergies, Type II hypersensitivities such as those present in Goodpasture's syndrome, myasthenia gravis, and autoimmune hemolytic anemia, and Type IV hypersensitivities such as those manifested in leprosy, tuberculosis, sarcoidosis and schistosomiasis. Degenerative nervous system diseases include, but are not limited to, multiple sclerosis and Alzheimer's disease.

Also intended as immune-related diseases as used herein are malignancies wherein the tumor cell carries a tumor marker, such as a tumor antigen, capable of being recognized and responded to by the immune system. The TCR can serve as a tumor marker on T cell leukemia or T cell lymphoma cells.

In addition to humans, other preferred animals for the present invention include domesticated animals such as equine, bovine, porcine, canine, feline and murine species. Autoimmune diseases in non-human species may be analogous to those identified in humans or may be uniquely characterized for a particular species or group of species. Thus, the methods of the present invention are useful in diagnosis and therapy in human and veterinary medicine.

5.2. ANTIBODIES OF THE INVENTION

The present invention is directed to an antibody, or a fragment, derivative, or analogue thereof, specific for an epitope of the V$\beta$3 region of a human TCR $\beta$ chain, preferably a human TCR $\beta$ chain, may be utilized in the diagnosis and therapy of an autoimmune disease, preferably RA. In a preferred embodiment, the antibodies are specific for the V$\beta$3.1 chain. The cDNA sequence for $\beta$3.1 is known (Concannon, et al., 1986, Proc. Nat'l. Acad. Sci. USA, 83:6548–6602) as are other V$\beta$3 subfamilies (Toyonaga et al., 1987, Ann. Rev. Immunol. 5:585–620). The antibodies of the present invention are useful in diagnosis and therapy.

The term "antibody" is meant to include polyclonal antibodies, monoclonal antibodies (mAbs), and chimeric antibodies (see below). (*Idiotypy in Biology and Medicine*, Academic Press, New York, 1984). Preferred antibodies are mAbs. Such antibodies may be of any immunoglobulin class including IgG, IgM, IgE, IgA, and any subclass or isotype thereof. Preferred antibodies for therapeutic use include antibodies of the IgG2a isotype or IgG2b isotype (Rashid et al., 1992, J. Immunol. 148:1382–1388).

The term "antibody" is also meant to include both intact molecules as well as fragments thereof which bind the antigen, such as, for example, $F(ab')_2$, Fab', Fab and Fv. These fragments lack the Fc fragment of an intact antibody molecule, clear more rapidly from the circulation, and may have less non-specific tissue binding than an intact antibody (Wahl et al., 1983, J. Nucl. Med. 24:316–325), properties which may be desirable for particular therapeutic or diagnostic utilities. It will be appreciated that these antigen-binding fragments of the antibodies useful in the present invention may be used for the detection and quantitation of TCR proteins or peptides as disclosed herein for intact antibody molecules. Such fragments are typically produced by proteolytic cleavage, using enzymes such as papain (to produce Fab fragments) or pepsin (to produce $F(ab')_2$ fragments) or by reducing the disulfide bridges.

The monoclonal antibodies of the invention are reactive with a variable region of the V$\beta$3 family of the beta chain of the T cell antigen receptor. In particular, such an anti-TCR$\beta$ mAb can recognize V$\beta$3.1. In a specific embodiment, the invention is directed to monoclonal antibodies 5E4 and 8F10, as deposited with the ATCC and assigned accession numbers HB 11020 and HB 11021, respectively. The V$\beta$3.1 specific monoclonal antibodies of the present invention enables the analysis of the expression of the V$\beta$3.1 gene in a biological sample.

Various chemical or biochemical derivatives of the antibodies or antibody fragments of the present invention can also be produced using known methods. One type of derivative which is diagnostically useful is an immunoconjugate comprising an antibody molecule, or an antigen-binding fragment thereof, to which is conjugated a detectable label such as a radioisotope or other tracer molecule. A therapeutically useful immunoconjugate comprises an antibody molecule, or an antigen-binding fragment thereof, conjugated to a therapeutically useful molecule such as a cytotoxic drug or a toxic protein (see, for review: Dillman, R. O., *Ann. Int. Med.* 111:592–603 (1989)). Such antibody derivatives are discussed in more detail below.

The antibody, fragment or derivative of the present invention, may be prepared by using any of a number of techniques well-known in the art. For producing a mAb, any method which provides for the production of antibody molecules by continuous cell lines in culture may be used. These methods include, but are not limited to, the hybridoma technique originally described by Kohler and Milstein (1975, Nature 256:495–497), and the more recent human B cell hybridoma technique (Kozbor et al., 1983, Immunology Today 4:72), EBV-hybridoma technique (Cole et al., 1985, *Monoclonal Antibodies and Cancer Therapy*, Alan R. Liss, Inc., pp. 77–96), and trioma techniques. A hybridoma of rodent origin producing the mAbs of this invention may be cultivated in vitro or in vivo. For an overview of antibody production methods, see: Hartlow, E. et al., *Antibodies: A Laboratory Manual*, Cold Spring Harbor Laboratory Press, Cold Spring Harbor, N.Y., 1988.

In one embodiment, the antibody of the present invention is a human mAb. Human mAbs may be made by any of a number of techniques known in the art (e.g., Teng et al., 1983, Proc. Natl. Acad. Sci. U.S.A. 80:7308–7312; Kozbor et al., supra; Olsson et al., 1982, Meth. Enzymol. 92:3–16).

In another embodiment, the antibody is a chimeric antibody, preferably a mouse-human chimeric antibody, wherein the heavy and light chain variable regions are derived from a murine mAb and the constant regions are of human origin. The chimeric antibodies of this invention have both the TCR-recognizing specificity of the mouse Mab and the biological properties of human antibodies, which include resistance to clearance in the human and lower immunogenicity for humans, allowing multiple treatments. Method for producing chimeric antibody molecules are disclosed, for example, in Gorman et al., PCT Pub. WO9206193 (Apr. 16, 1992); Cabilly et al., U.S. Pat. No. 4,816,567 (Mar. 28, 1989) and Eur. Patent Pub. EP125023 (Nov. 14, 1984); Taniguchi et al., Eur. Patent Pub. EP171496 (Feb. 19, 1986); Morrison et al., Eur. Patent Pub. EP173494 (Mar. 5, 1986); Neuberger et al., PCT Pub. WO8601533 (Mar. 13, 1986); Kudo et al., Eur. Patent Pub. EP184187 (Jun. 11, 1986); Robinson et al., PCT Pub. WO 8702671 (May 7, 1987); Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Morrison, *Science*, 229:1202–1207 (1985); Neuberger et al., *Nature* 314:268–270 (1985); Takeda et al., *Nature* 314:452–454 (1985); Oi et al., *BioTechniques* 4:214 (1986); and Liu et al., *Proc. Natl. Acad. Sci. USA* 84:3439–3443 (1987).

For human therapeutic purposes, mAbs or chimeric antibodies can be "humanized" by producing human constant region chimeras, where even parts of the variable regions, in particular the conserved or framework regions of the antigen-binding domain, are of human origin, and only the hypervariable regions are non-human. See for example, UK Patent Publication GB 2188638 A entitled "Chimeric Antibodies", Harris et al., PCT Publication WO 9204381, published Mar. 19, 1992, entitled "Novel Antibodies for Treatment and Prevention of Infection in Animals and Man," and Riechmann et al, 1988, Nature 332:323–327.

In a further embodiment, the antibody is a single chain antibody formed by linking the heavy and light chain fragment of the Fv region via an amino acid bridge, producing a single chain polypeptide (Bird, 1988, Science 242:423–426; Huston et al, 1988, Proc.Natl.Acad.Sci. USA 85:5879–5883; and Ward et al, 1989, Nature 34:544–546).

Antibody molecules or fragments may be purified by known techniques, e.g., immunoabsorption or immunoaffinity chromatography, chromatographic methods such as HPLC (high performance liquid chromatography), or a combination thereof, etc.

Once antibodies of the desired specificity are generated, they may be used to identify and select other antibodies having the same or cross-reactive epitope specificity. For example, a new antibody is tested by measuring its ability to inhibit the binding of an antibody of known specificity to its epitope. Various competitive binding assays known in the art can be used.

The isotype of the antibody can be selected during hybridoma production or by appropriate recombinant methods well-known in the art to achieve a desired effector function mediated by the Fc portion of the immunoglobulin heavy chain. For example, certain isotypes, such as IgG2a, have superior activity in antibody-dependent cellular cytotoxicity. Likewise, certain isotypes, such as IgG2a, are more readily eliminated from the circulation through Fc receptors on cells of the reticuloendothelial system and are therefore more efficient at removing an undesired antigen or target cell from sites of active disease (Rashid, et al., 1992. J. Immunol. 148: 1382–1388). Accordingly, depending on the intended use, a particular antibody isotype may be preferable to others, as can be readily ascertained by one of ordinary skill in the art without undue experimentation.

To identify a hybridoma producing an antibody of a particular isotype, or to switch an isotype of an antibody, the hybridoma supernatants may be screened for production of TCR-specific mAbs using an ELISA which tests for the immunoglobulin isotype. What follows is an example of a method for selecting a desired isotype switch from IgG1 to IgG2a. Hybridoma cells are grown in the logarithmic phase for a 2–3 week period prior and then subjected to negative selection using antibody-coated magnetic beads. Super paramagnetic iron oxide particles coated with a goat anti-mouse antibody preparation including all IgG isotype classes (Biomag® beads purchased from Advanced Magnetics, Inc.) may be used. For switching an isotype from IgG1 to IgG2a, it is necessary to block the IgG2a binding sites on the antibody-coated beads by incubating with immunoglobulins (of irrelevant specificity) having the IgG2a isotype. About $10^8$ hybridoma cells expressing a variety of isotypes are incubated with such IgG2a-blocked beads. Cells expressing IgG1, IgG2b and IgG3 isotypes bind and are removed magnetically from the population. Such a negative selection step is preferably repeated several times.

The remaining cell population, depleted of IgG1, IgG2b and IgG3 bearing cells, and conversely enriched for IgG2a-bearing cells, is plated in microplates at a cell density of about 1000 cells/well. Using commercially available anti-isotype reagents in an ELISA assay, the wells are screened for IgG2a production; positive clones are replated at 0.3 cells/well followed by another round of screening and re-plating. Using such an approach, approximately 1–5 of $10^7$ cells which have switched isotype are optimally selected. Cells which have switched from IgM to IgG can be selected using a similar approach with the appropriate antibody-coated beads.

As used herein, an antibody reactive with the "V region" of the TCR shall be construed to be an antibody reactive with an epitope of the V region, a combination epitope of the V region, or a combination epitope of the V-D or V-D-J regions. An antibody reactive with a V region of a TCR may recognize an idiotypic determinant, a clonotypic determinant, or, preferably, may recognize a minor framework region expressed by a discrete subset of T lymphocytes. Preferably, such an antibody is reactive with a unique epitope on a Vβ3.1 variable region of the β chain of the T cell antigen receptor.

The term "minor framework region" refers to a region of the TCR which is not shared by all TCR molecules, but is also not unique to a particular T cell clone. Preferred anti-TCR β mAbs recognize members of the Vβ3 family, most preferably, Vβ3.1.

5.3. METHODS OF GENERATING AND CHARACTERIZING ANTIBODIES OF THE INVENTION

This invention provides specific monoclonal antibodies reactive with defined regions of the members of the Vβ3 family variable regions of the β T cell antigen receptor. Over the last several years, since the cloning of the genes encoding for the TCR, surprisingly few antibodies have been generated against the different variable, diversity, joining or constant regions of the receptor. This indicates that the knowledge of the amino acid sequence of a particular region of interest has not been sufficient to allow the reproducible production of specific antibodies. Several groups have been able to generate one or two specific antibodies, but no one seems to have been able to generate antibodies at will. Over several years, Present inventors have generated several TCR antibodies by numerous methods and now have a preferred method to maximize success in generating antibodies against a defined region of interest.

The major elements of this improved protocol include 1) the use of purified protein as the preferred immunogen; 2) effectively monitoring the mice by tailbleeds and prescreening during immunization to detect positive antibody responses; 3) using purified protein during the screening of hybridoma supernatants to minimize the number of hybridomas to be screened to detect positive ones and to maximize the positive signal over background in the screening procedure so that true positives are not missed due to weak signals; and 4) better characterizing the resultant positives to determine their true specificity.

5.3.1. HOST REQUIREMENTS

Various host animals, including but not limited to mice, rats or rabbits can be used in the practice of this invention. However, some hosts are preferred, as discussed infra. Several years of experience in generating TCR antibodies has resulted in the observation that the TCR proteins are not very immunogenic. This is perhaps due to the pivotal role the proteins themselves play in the immune system. Only those TCRs that recognize "non-self" are allowed to exit the thymus during ontogeny. In addition, the proteins are highly conserved evolutionarily and are members of the immunoglobulin supergene family. Members of this supergene family share not just sequence homologies, but structural similarities as well. It is now known that some human-mouse homologs exist that are very similar in sequence (Wilson et al., 1988, Immunol. Reviews 101: 149–172). This was first proposed as the variable genes were being mapped for their relative position along the chromosome (Lai et al., 1988, Nature 331: 543–546). Thus, some human Vβ and murine Vβ sequences are more similar to one another than either one is to other variable regions in the species. The practical result of this similarity is that human TCR proteins used as immunogens in mice to produce an antibody response yield variable results. It generally takes several weeks or months to generate a response in the mice, requiring multiple boostings. Although a better immune response may be generated in other hosts, chickens, for example, the lack of reliable myeloma fusion partners needed to create the immortal fused hybridomas for chicken spleen cells limits the usefulness of these hosts.

In order to maximize the antibody response in mice to human immunogens, various groups have proposed using host animals deficient in the TCR homolog of interest. For example, mice strains such as SJL, RIII S/J (H-2'), C57L, C57BR and SWR (Behlke et al., 1986, Proc. Natl. Acad. Sci USA 83:767–771; Haqqi et al., J. Exp. Med., 1989, 169: 1903–1909; Jouvin-Marche, 1989, Eur. J. Immunol. 19: 1921–1926) that have deleted major portions of the murine Vβ locus may be advantageous for generating antibodies against the corresponding human homologs. Other murine strains such as nude mice or SCID mice may be useful for similar reasons. Taking this idea one step further, one group has proposed genetically engineering mouse cells to produce a chimeric TCR where every portion of the TCR is murine, except the portion (e.g. the human variable region) to be used to elicit antibodies. This procedure has worked in at least one instance to generate Vβ13.1 and Vβ13.2 specific antibodies (Intl. Publ. No. WO92/02629, published Feb. 20, 1992), but is not the complete answer to the problem of creating antibodies at will, for the reasons indicated below under screening.

5.3.2. PREFERRED IMMUNOGENS

There are a large number of different immunogens representing defined regions of the TCR that can be used to generate antibodies. Some of these include peptides; conjugated peptides; partially purified TCR protein by immunoprecipitation, for example; more fully purified protein; T cell clones; transfected cells; soluble recombinant receptor protein; or combinations of these. TCR antibodies that exist today have been generated on a hit-or-miss basis for each of these immunogens. However, a careful understanding of the relative merits of each immunogen was necessary in order to develop the present inventors' preferred procedure to yield a desired antibody.

Peptide immunogens: Several groups have used chemically synthesized TCR peptides to generate numerous anti-peptide antibodies to TCR. Unfortunately, these anti-peptide antibodies very rarely interact with intact receptor on cells. Thus, they have no therapeutic or in vivo diagnostic utility. Often such anti-peptide antibodies react well with the peptide to which they were raised, but react poorly with TCR proteins, even when the protein is denatured, by Western blotting for example. Further complications include the observations that not all peptides are soluble and that the peptides sometimes lack the carbohydrate groups present on the native version of the receptor. In summary, although anti-peptide antibodies can be generated, the resulting antibodies often have little utility for diagnostic and therapeutic applications, and the use of peptides as immunogens has not given rise to anti-minor framework or V region specific antibodies.

Whole Cell Immunogens: Immunogen on the surface of T cells or on transfected T cells have been used to generate specific antibodies. Various cell lines including, but not limited to, those disclosed herein and cell lines disclosed elsewhere (see, for example, Toyonaga et al., 1987, Ann. Rev. Immunol. 5:585–620) can be used as immunogens to generate mAbs specific for the human TCR V region. Any T cell line expressing a TCR, a TCR chain or fragment on the cell surface may serve as an immunogen. Note that antibodies to known V, D, J, DJ, VJ, VDJ or combinations thereof can also be generated by immunizing with such cells.

The expression of DNA encoding the V, D, J, and C regions of any TCR chain can be determined in any cell line by well-known procedures including cDNA sequencing, in situ hybridization, polymerase chain reaction (PCR) analysis, Northern analysis, Southern analysis, immunoassay, or flow cytometry cytometry, to name but a few. The V specificity of the resultant antibody can be determined from knowing the sequence of the TCRs expressed by the immunizing cell.

Whole cells that can be used as immunogens to produce a TCR-specific antibodies of the present invention include not only T cells which naturally express a TCR, but also cells transfected with a recombinant DNA construct which encodes a particular TCR chain or chains, or a fragment thereof. For example, β⁻ Jurkat cells which do not produce a functional TCR can be "reconstituted" by transfection with TCR β cDNA to produce intact αβ TCR on the cell surface (Ohashi, P. S. et al., Nature, [1985] 316:606–609). Such transfected cells would then be used as immunogens for inducing antibodies specific for an α or β TCR epitope. Additional examples of such transfected cells have been reported (Kaye, J. et al., 1988, Nature 336:580–583; Dembic, Z., et al., 1986, Nature 320:232–238; Saito, T., et al., 1987, Nature 325:125–130). According to the present invention, any procedure that results in expression of a transfected TCR gene on the cell surface could be used to produce a whole cell immunogen.

Immunogens can also be produced as proteins or cells derived from eukaryotic expression systems in which a TCR protein or peptide is attached to the cell membrane via an enzymatically cleavable phospholipid anchor domain (Int'l Patent Application PCT/US88/02648, published Feb. 9, 1989).

Many of the antibodies produced using these whole cell immunogens are anti-idiotypic or anti-clonotypic, but some anti-minor framework or variable region specific antibodies have been generated, as well. Although not impossible, it is rare that anti-constant region antibodies are produced using whole cell immunogens, since the constant regions of the TCR chains appear to be masked by one another and by T3 polypeptides also present in the TCR:T3 complex on the surface of cells.

The major drawback of using cells as immunogen for producing anti-TCR antibodies is that many other non-TCR proteins on the cell are also immunogenic. The antibodies specific to the TCR represent a minor subset of the total antibody response generated in the host. As a result, large numbers of hybridomas need to be screened to detect the ones producing TCR specific antibodies. Even when the cells used to immunize are murine cells expressing only one defined human region, the screening procedure is not optimal. For example, in order to prescreen the mice to determine if they are making specific antibody prior to isolation of the spleen cells and fusion with the myeloma partner, it is necessary to try to titrate mouse serum by dilution until it is possible to see the difference between a negative versus a positive result. Since mouse serum has an extremely high protein concentration, the difference in a positive hybridoma supernatant can not always be seen above the background created from the serum itself. When hybridoma supernatants are screened by Flow cytometry analysis by detecting binding to the same transfected cells used as immunogen or by their ability to generate an IL-2 response, the same problem of detecting a positive difference over the background of the testing procedures exist. The observed signals are small relative to the background ones.

Purified Protein Immunogens: When purified protein is used as an immunogen, a less heterogeneous, more efficient antibody response is generated in the host. This results in an increased relative proportion of cells producing antibodies against the desired TCR antigens over the other contaminating antigens present in the immunogen. This is especially important for enhancing TCR specific antibody responses, since TCR are not very immunogenic to begin with. In addition, an increased proportion of desired cells minimizes the number of hybridoma cells that must be screened to find positives. The "purer" the protein used as immunogen, the better the chances for success. Present inventors prefer using purified, soluble, recombinant protein as immunogen, if available, since a large quantity of material is available to use first as immunogen and later in improved prescreening and screening procedures. With a purified protein it is possible to maximize the signal to noise ratio of the prescreening and screening methods, so it is easier and more reliable to detect positive hybridomas over assay background. A purified protein can also be used to generate all types of TCR antibody, e.g. it is possible to identify anti-idiotypic, anti-variable or anti-minor framework, and anti-constant or anti-major framework specificities.

The present invention in a preferred embodiment thus uses a soluble Vβ3 TCR polypeptide that can be used 1) as immunogen to generate specific antibodies and 2) in screening protocols to enhance signal to background ratios to identify and characterize said antibodies.

5.3.3. IMPROVED SCREENING PROCEDURES

Screening procedures that can be used to screen hybridoma cells expressing different anti-TCR antibodies include but are not limited to (1) enzyme linked immunosorbent assays (ELISA), (2) flow cytometry analysis, (3) immunoprecipitation, (4) Western blotting and (5) the ability to comodulate the CD3 antigen (part of the TCR-CD3 complex present on the surface of the T cells) off of the surface of cells. The comodulation and flow cytometry screening procedures are preferred for the selection of antibodies potentially useful in therapy since these procedures select antibodies that are able to recognize intact TCR on live cells.

Many different immunoassay formats including but not limited to ELISA, EIA, and RIA formats of an ELISA that can be used to screen for anti-TCR antibodies as can be envisioned by one skilled in the art.

Many additional screening assays, such as those based upon competition with anti-TCR antibodies of known specificity or the ability to cause T cells expressing known TCRs to proliferate in culture, will be known to those skilled in the art and can be used for the selection of appropriate antibodies.

Initially it was difficult to obtain antibodies reactive with T cell receptor V regions. This problem arose when the signal observed by the antibody binding to PBLs by flow cytometry analysis was very low relative to the background of Flow cytometry itself. Since this signal to background level was so low, and was many times obscured by the variability of the assay itself, it was concluded that the antibodies were reacting positively only with the T cell clone used to generate them. As more became known about the number of T cell receptor genes for the β chain (60–100 total human genes in about 20 variable region families) and the a chain (100 or so human genes), it was easier to interpret the flow cytometry data more accurately. For example, a Vβ region specific antibody would be expected to react with about 5% of PBLs on average. Later studies of the percentages of families of Vβs in normal PBLs indicate that families are actually present at 1% to 8% depending upon the individual family. Depending upon the actual instrument, its calibration, the skill of the operator and the inherent interassay variability of flow cytometry analysis, background levels in flow cytometry can easily be in the 3–4% range. Thus, ironically, the same problem that confounded investigators trying to make specific TCR antibodies 7–8 years ago still exists today: the ability to distinguish a true positive hybridoma by a screening method is diminished in assays that provide low signals with high backgrounds.

Present inventors have improved the chances of success of identifying desired hybridomas, by providing improved screening assays with greater signal to noise ratios. One such assay is an ELISA format using purified protein, better yet purified soluble, recombinant protein, to bind to antibodies in hybridoma supernatants to generate strong positive signals. Since the "analyte" in these assays is a known, purified protein, the signals are higher than those obtained if cell lysates or other partially purified protein preparations containing numerous contaminants are used. These more effective and efficient screening assays enhance the ability to prescreen mouse serum to monitor effective antibody responses in the host following immunization and to screen pooled hybridoma supernatants during initial screening of many hybridoma candidates. Another advantage of the ELISA assays is that the choice of the plating antibody (pan-Ig or IgG2b specific, for example) can positively select for TCR specific antibodies of a preferred isotype. Thus, once a desired TCR antibody is identified, it is not necessary to then switch its isotype. With soluble, purified protein it is also possible to bind antigen directly to the plate rather than using sandwich immunoassay formats.

5.3.4. IMPROVED CHARACTERIZATION PROCEDURES

After a positive hybridoma has been detected by the initial screening protocol, it is then further screened and analyzed to determine its specificity. Such characterization includes, for example 1) immunoprecipitation followed by SDS gel electrophoresis to determine if the antibody precipitates proteins of sizes expected for TCRs, with or without coprecipitation of the T3 polypeptides; 2) the ability of the antibody to comodulate the T3 receptor off the surface of cells, indicating that the antibody is reacting with the TCR; 3) determining the percentage of CD3 positive PBLs the antibody binds to by flow cytometry analysis to determine whether it is anti-idiotypic, anti-variable or anti-constant region specific; 4) Western blot analysis to determine β chain specificity, 5) blocking experiments with other known antibodies or peptides to determine epitope specificity or similarity to known antibodies; and 6) analysis against a panel of cells expressing known TCRs to determine variable or constant region reactivity.

In addition to these procedures the present inventors have found that the following procedure allows even better antibody characterization. Once an antibody has been generated and characterized as indicated above, it is then used to stimulate PBLs to expand in culture. The antibody specifically interacts with the subset of PBLs expressing the epitope reactive with the antibody and stimulates a mitogenic response. As cycles of this mitogenic response occur, the antibody is selectively amplifying these cells until it is possible to generate cell lines that are up to 95% reactive with the antibody. This results in a very high positive signal that it easy to distinguish over background, for example a 95% positive signal in flow cytometry over a background signal of 2–4%. Using this procedure it was possible to distinguish the true specificity of antibody W112 (Vβ5.3) over antibody 1C1 (Vβ5.2 and Vβ5.3) (Boylston et al., 1986, Immunol. 137(2): 741). In addition, the present inventors were able to determine the fine specificity of antibodies 5E4 and 8F10 as being variable region specific and not a combined variable and joining region specificity. A further advantage of this amplification method is that it is simple to distinguish a true anti-idiotypic antibody from one that recognizes one of the less expressed V region families. The anti-variable region antibody will productively drive PBLs through mitogenic cycles to generate an amplified cell line. Since it is extremely unlikely that an anti-idiotypic antibody will find its cognate antigen in a population of PBLs, it will not generate amplified cell lines.

The present inventors have further characterized the ability of specific antibodies to interact with monkey cells, e.g. the presence of a monkey homolog. Since anti-human TCR antibodies do not cross react with non-primate TCR, an important advantage of the present invention is to enable a primate model for safety, toxicity and efficacy studies. While some anti-TCR V Region antibodies react with monkey cells and others do not (See Axberg et al., 1991, J. Clin. Immunol. 11, 1–12), the present inventors have shown that 5E4 and 8F10 do react with monkey cells. It is possible to further define the fine specificities of these antibodies, since similar antibodies by other characterization procedures may interact with different percentages of monkey cells. Thus, although they recognize similar antigens, they may recognize different epitopes or combined epitopes.

5.4. DIAGNOSTIC UTILITY OF THE ANTIBODIES OF THE INVENTION

The antibodies and fragments of the present invention can be employed for diagnostic or research purposes in various immunoassays well-known in the art. The antibodies, or fragments of antibodies, useful in the present invention may be used to quantitatively or qualitatively detect the presence of cells which express a member of the TCR Vβ3 family, particularly Vβ3.1, or the levels of TCR protein present in a sample. This can be accomplished by immunofluorescence techniques employing a fluorescently labeled antibody (see below) coupled with light microscopic, flow cytometry cytometric, or fluorimetric detection.

The antibodies (or fragments thereof) useful in the present invention may be employed histologically, as in immunofluorescence or immunoelectron microscopy, for in situ detection of the TCR molecule.

One way of measuring the reactivity of a T cell receptor epitope with a specific antibody of the present invention is by enzyme immunoassay (EIA) such as an enzyme-linked immunosorbent assay (ELISA) (Voller, A. et al., *J. Clin. Pathol.* 31:507–520 (1978); Butler, J. E., *Meth. Enzymol.* 73:482–523 (1981); Maggio, E. (ed.), *Enzyme Immunoassay*, CRC Press, Boca Raton, Fla., 1980). The enzyme, either conjugated to the antibody of the invention, or to a binding partner for the antibody, when later exposed to an appropriate substrate, will react with the substrate in such a manner as to produce a chemical moiety which can be detected, for example, by spectrophotometric, fluorimetric or by visual means.

A preferred method of enumerating total T Cell receptor β chain or total V region subset TCR chain is performed using detergent treated whole blood samples. In particular Vβ3.1 subset may be detected from a sample. Whole or whole blood samples are added to wells in a 96 well plate previously coated with 5 μg/ml of coating antibody. Coating antibody is either a negative control, an anti-major framework antibody such as W76 (to detect total β chain) or a TCR V region specific monoclonal antibody such as those of the present invention (to detect a subset of TCR β chain). An HRP conjugated BF1 antibody, which recognizes a different epitope of the β chain C region than W76 is used as a detection antibody. The assay can be used to detect total TCR β chain as well as β chain subsets such as Vβ3.1. The assay format is described in Rittershaus C. W. PCT Publication WO9208981, published May 29, 1992 entitled, "Therapeutic and diagnostic methods using total Leukocyte surface antigens."

Detection of a member of the TCR Vβ3 family protein or cells may be accomplished using any of a variety of other immunoassays. For example it is possible to detect antibody binding to TCR V region through the use of a radioimmunoassay (RIA) (see, for example, Weintraub, B., *Principles of Radioimmunoassays*, Seventh Training Course on Radioligand Assay Techniques, The Endocrine Society, March, 1986, pp. 1–5, 46–49 and 68–78; Work, T. S. et al., *Laboratory Techniques and Biochemistry in Molecular Biology*, North Holland Publishing Company, New York, 1978).

It is also possible to label the antibody in which binding is measured using radioactive, fluorescent, chemiluminescent or bioluminescent conjugated antibodies.

A variety of immunoassay formats is available, for either EIA or RIA systems. For example, assays may be competitive or non-competitive. Two site or sandwich assays may be used, either "forward", "simultaneous" or "reverse" assays, which are well-known in the art.

Additional types of immunoassays include precipitin reactions, gel diffusion precipitin reactions, immunodiffusion assays, agglutination assays, complement fixation assays, immunoradiometric assays, protein A immunoassays, and immunoelectrophoresis assays.

Binding of the antibody, or fragment or derivative thereof to the TCR epitope for which it is specific may be accomplished and/or detected in vitro or in vivo. In vitro binding, as described above, may be performed using histologic specimens, or fractions or extracts of tissue or fluid, including substantially purified T cells. In vivo binding may be achieved by administering the antibody (or fragment or derivative) by any route or means known in the art, including but not limited to intravenous, intraperitoneal, intranasal, and intraarterial, such that specific binding may be detected.

For diseases involving joints, such as RA, intraarticular administration of a labelled antibody (or derivative or fragment) may also be utilized as a diagnostic procedure.

Imaging techniques can be used in vivo, wherein the antibody, derivative or fragment is bound to a detectable label capable of in vivo localization. Many different labels and methods of labeling are known in the art.

The present invention provides method for diagnosing an immune-related disease, including a lymphatic malignancy, based on detecting the specific binding of a mAb, or a derivative or fragment thereof, to a defined region of a TCR in a biological sample from a subject suspected of having the disease or disorder. Biological samples which may be tested according to the present invention include any body fluid, such as peripheral blood, plasma, cerebrospinal fluid, lymph, peritoneal fluid, or pleural fluid, and the like, or any body tissue or extract thereof.

According to the present invention, RA may be diagnosed in a subject by detecting the increased presence of T cells expressing Vβ3, in particular, Vβ3.1, alone or concomitant with increased presence of T cells expressing Vβ9, or Vβ10, in a biological sample from the subject as compared to baseline samples. Such diagnosis may be achieved by the use of a mAb, fragment or derivative, specific for the particular TCR V region associated with the disease, as described above. As used herein, the term "baseline sample" refers to a sample from a normal, healthy individual who does not have rheumatoid arthritis, or a sample from the subject prior to onset of the disease or at a time of remission of the disease. In a further aspect, a baseline sample may be a mixture or average of samples from a general population. In a special embodiment the biological sample being tested in from the site of disease and the base line is the peripheral blood.

Alternatively, such diagnosis may be achieved by detection of the presence of nucleic acid sequences characteristic of these TCR V regions using molecular techniques. Preferably, such molecular diagnosis is achieved by detecting the presence of nucleic acid sequences homologous to a gene encoding a defined TCR or Vβ3, preferably Vβ3.1, region in mRNA in a patient sample. The nucleic acid and amino acid sequence for the Vβ3 gene family members and gene products are known (Toyonaga et al., 1987 Ann. Rev. Immunol., 5:595-620). One skilled in the art could readily design diagnostic tests to detect the Vβ3 elevation described here. Molecular approaches used to correlate TCR gene expression with disease include:

(1) producing and analyzing cDNA libraries obtained from the disease-related T cells obtained from one or more subjects having the disease, to determine the presence of frequently used or "dominant" TCR genes;

(2) Southern analysis of disease samples to determine whether specific genetic polymorphisms (e.g., RFLPs) or oligoclonal TCR rearrangements exist;

(3) analysis of disease samples by cDNA synthesis, PCR amplification, and slot blot hybridization procedures, described in more detail below; this procedure requires less time and allows testing of a larger number of patients;

(4) in situ nucleic acid hybridization of TCR probes to T cells without prior culture of these cells.

It should be understood that the diagnostic methods of the present invention are best used along with other known diagnostic methods to obtain a comprehensive patient diagnosis. For example, a diagnosis of RA may be made based on the methods of the present invention together with conventional diagnostic recognition of the clinical features of RA, such as:

(a) typical joint involvement (chronic, symmetrical arthritis);

(b) early involvement most often in the hands;

(c) characteristic radiographic features;

(d) presence of rheumatoid factor;

(e) presence of rheumatoid nodules, etc. See, for example, Fishman et al., Medicine, Second Ed., J. B. Lippincott Company, Philadelphia, Pa., pp. 340-346. As with any diagnostic criteria, the parameters disclosed in the present invention may not be sole determinants, or pathognomonic, of a particular disorder.

5.5. THERAPEUTIC UTILITY OF THE ANTIBODIES OF THE INVENTION

As mentioned above, the present invention is also useful in the therapy of an immune-related disease, preferably an autoimmune disease or a lymphatic malignancy. The therapeutic embodiments of the present invention are best applied once a correlation has been established between a disease of interest, for example RA, and preferential use of a particular TCR V gene in T cells associated with the disease, for example genes encoding a member of the Vβ3 family, in particular Vβ3.1, alone or concomitant with use of genes encoding Vβ9, or Vβ10.

The particular TCR which is expressed on or "marks" those T cells mediating the autoimmune process is designated, a "marker TCR." In a preferred embodiment, the marker TCR for rheumatoid arthritis is Vβ3.1. The antibodies, fragments or derivatives of the present invention are therapeutically useful in part because of their ability to interfere with the binding of the T cell, via its TCR, to the MHC/antigen complex (or the antigen alone) needed for initiation or propagation of the autoimmune process.

Marker TCRs associated with a given disease are identified using any of a variety of techniques well-known in the art. Marker TCR V genes for RA are exemplified in more detail below. A genetic approach using patients known to have Myasthenia gravis or multiple sclerosis was described by Oksenberg, J. R., et al., Proc. Natl. Acad. Sci. USA 86:988-992 (1989). Sequences of the appropriate TCR β chain are obtained by genomic analysis using restriction fragment length polymorphisms found in families having a prevalence of the particular autoimmune disease, for example, as described by Seboun, E., et al., Cell 87:1095-1100 (1989); Burns, F. R., et al., J. Exp. Med. 169:27-39 (1989)). Thus it is within the level of ordinary skill in the art to identify other diseases associated with expression of Vβ3, in particular Vβ3.1.

It should be appreciated that, for the purposes of the present invention, determination of the marker TCR associated with an autoimmune disease does not require that the "autoantigen" be characterized. It is sufficient that the autoimmune disease involves a T cell-mediated immune response as a necessary part of the pathogenetic process. In fact, as is known in the art, the autoimmune disease may not involve a true autoantigen at the inductive stage, but rather, may represent a response to an exogenous antigen, such as a bacterial or viral antigen, which is cross-reactive with self antigens, or results in an immunopathologic response directed to the exogenous antigen present in the host.

T cells of the subset associated with the autoimmune disease, which may recognize a true autoantigen or an autoimmune disease-associated antigen (such as certain viral or bacterial antigens) may be cloned and expanded or immortalized in culture by methods well-known in the art. For example, the T cells may be fused to an immortalizing cell, e.g., a long term T cell line, a T cell lymphoma line or a T cell hybridoma, and then grown in culture. The cultured cells serve as the source of cell-surface TCR chains which are analyzed using the antibodies of the present invention, or as the source of cDNA encoding the appropriate TCR for molecular identification of TCR usage. Such CDNA is cloned and expressed by methods well known in the art.

(See, for example, Sambrook, J. et al. (*Molecular Cloning: A Laboratory Manual*, 2nd Edition, Cold Spring Harbor Press, Cold Spring Harbor, N.Y. (1989)). T cells may be isolated from humans who are susceptible to an autoimmune disease, preferably from susceptible individuals who have the autoimmune disease, and are expanded in culture using known techniques (see, for example, Zamvil et al., *Nature* 317:355–358 (1985); *Nature* 324:258–260 (1986)).

An absolute correlation between an autoimmune disease and the usage of a particular TCR is neither expected nor necessary for every individual to successfully practice the present invention. Correlations have been shown for some individuals with Rheumatoid arthritis and the expression or presence of Vβ3 in the synovial tissue relative to peripheral blood. The correlation also exists for increased expression of Vβ9 or Vβ10 relative to peripheral blood, or both, especially when detected in addition to Vβ3.

The TCR expressed by T cells specifically associated with a disease can be identified using TCR-specific antibodies, either polyclonal, monoclonal or chimeric, such as those described herein. Specifically antibodies for an epitope of a member of the TCR Vβ3 family, specifically Vβ3.1, can be used to detect surface expression, employing techniques of fluorescence microscopy, flow cytometry cytometry, immunocytochemistry, or other techniques known in the art. Such antibodies are described herein, and have been reported by others for a number of TCR αβ chain V regions in rodent systems (See, for example, Ohashi, M., et al., *J. Exp. Med.* 168:2153–2164 (1988); Gascoigne, N. R. J., et al., *Proc. Natl. Acad. Sci., USA* 84:2936 (1987); Kappler, J. W., et al., *Nature* 332:35 (1988); Kappler, J. W., et al., *Cell* 49:263 (1987); MacDonald, H. R., et al., *Nature* 332:40 (1988)).

As an alternative to analysis of the cell surface using antibodies, DNA or MRNA of the T cells can be probed directly, or after amplification by the polymerase chain reaction (Synha et al., *Science* 239:1026 (1988); Saiki et al., *Nature* 324:163 (1986), by specific hybridization with nucleic acid probes for the various TCR gene families, using hybridization methods well known in the art (See examples, below).

Where no specific autoantigen has been identified, the oligoclonality of T cells in the anatomic region associated with the disease can be used as a basis for enrichment of reactive T cells. For instance, cells uniquely associated with RA are found in the synovial fluid of the joint; cells uniquely associated with MS are found in the cerebrospinal fluid (CSF); and disease-associated T cells infiltrate the thyroid tissue in Hashimoto's thyroiditis and in Graves' disease. In these instances, T cells may be isolated from the relevant anatomical location and expanded in culture. (See, for example, Londei, M. et al., *Science* 228:85–89 (1985); Stamenkovic, I. et al. *Proc. Natl. Acad. Sci. USA* 85:1179–1183 (1988); Oksenberg, J. R., et al., supra).

Treatment of an individual using the antibodies, fragments or derivatives of this invention comprises parenterally administering a single dose or multiple doses of the antibody, fragment or derivative. The effective dose is a function of the individual antibody (or fragment or derivative), the presence and nature of a conjugated therapeutic agent, the subject and his clinical status. Effective doses of the antibodies, fragments or derivatives of this invention for use in preventing, suppressing, or treating an immune-related disease are in the range of about 1 ng to 100 mg/kg body weight. A preferred dose range is between about 10 ng and 10 mg/kg. A more preferred dose range is between about 100 ng and 1 mg/kg.

The route of administration may include intravenous (IV), subcutaneous (SC), intramuscular, intrapulmonary, intraperitoneal (IP), intranasal, intracerebroventricular, intrathecal, intradermal, or other known routes.

As mentioned above, the antibody or antigen-binding fragment thereof can be coupled to cytotoxic proteins, including ribosomal inhibitory proteins such as Ricin-A, Pseudomonas toxin, and Diphtheria toxin, as well as other proteins such as tumor necrosis factor. Toxins conjugated to antibodies or other ligands, are known in the art (see, for example, Olsnes, S. et al., *Immunol. Today* 10:291–295 (1989)). Since antibody to a TCR epitope will react with a much smaller proportion of total lymphocytes than the more broadly-reactive immunotoxins used to date, higher doses of a toxin-conjugated anti-TCR antibody will be tolerated by patients, or conversely, lower doses will be effective.

In a preferred embodiment, ricin A chain is conjugated to a TCR-specific antibody of the present invention, i.e., an anti-Vβ3 antibody, resulting in an immunoconjugate capable of binding to the TCR of lymphocytes which are a causative agent of an autoimmune disorder, such as RA, and destroying the cells, thereby treating the disease. Effective doses of a ricin A conjugated monoclonal anti-TCR antibody are in the range of about 0.005 to 0.5 mg/kg/day, with the preferred dose in the range of about 0.05 to 0.2 mg/kg/day.

The anti-TCR antibodies of this invention can be conjugated to additional types of therapeutic moieties including, but not limited to, radionuclides and cytotoxic drugs, to treat individuals with autoimmunity or with malignant or lymphoproliferative disease. Non-limiting examples of radionuclides which can be coupled to antibodies and delivered in vivo to sites of antigen include $^{212}$Bi, $^{131}$I, $^{186}$Re, and $^{90}$Y. Such radionuclides exert their cytotoxic effect by locally irradiating the cells, leading to various intracellular lesions, as is well-known in the art of radiotherapy.

Cytotoxic drugs which can be conjugated to antibodies and subsequently used for in vivo therapy include, but are not limited to, daunorubicin, doxorubicin, methotrexate, and mitomycin C. For a fuller exposition of these classes of drugs which are known in the art, and their mechanisms of action, see Goodman, A. G., et al., *Goodman and Gilman's The Pharmacological Basis of Therapeutics*, 7th Ed., Macmillan Publishing Co., (1985).

The therapeutic approaches disclosed herein are based on any of a number of possible mechanisms by which the antibodies, fragments or derivatives of the present invention may act to achieve the therapeutic benefits. The present inventors do not intend to be bound by any particular theory as to mechanism of action.

In one embodiment, if a particular Vβ3 TCR-specific antibody is capable of inducing T cell proliferation in vitro (see Examples, below), it may be administered therapeutically to induce activation and/or proliferation of T cells bearing a member of the Vβ3 TCR family, leading to specific cell-mediated immunity.

In another embodiment, an antibody directed against a marker Vβ3 TCR associated with disease-causing T cells can be used, alone or conjugated to a toxic agent, to remove the undesired T cells.

In yet another embodiment, the Vβ3 TCR-specific antibody is administered therapeutically to block the interaction of effector T cells with the antigen for which they are specific, thereby modulating a deleterious immune response.

An administered antibody, fragment or derivative of the present invention may act by binding a Vβ3 TCR molecule in vivo and marking the T cell bearing that Vβ3 TCR for elimination by the one or another host defense system such as the reticuloendothelial system, or through antibody-dependent cellular cytotoxicity.

Typically, when the antibody is used to stimulate the T cell subpopulation bearing the particular Vβ3 TCR, the antibody is administered at a lower concentration known as a "mitogenic" concentration. When the antibody is being used for T cell elimination, it is administered at a much higher concentration.

For the antibody, fragment or derivative of the present invention to be useful in therapy, it must have the ability to recognize and either modulate or lead to the destruction of a specific disease-related T cell subset. The exact nature of this therapeutic modulation, whether by stimulation, blocking, or elimination of T cells, depends upon the disease being treated and the nature of the specific T cell subset(s) involved.

First generation treatments based on anti-Vβ3 TCR antibody therapeutics may be developed using knowledge of the correlation between a disease and the expression of a specific TCR Vβ3 region gene subfamily in subjects having the disease. Such therapeutics offer an improvement over known procedures, such as the use of anti-CD3 antibody in the treatment of renal transplant rejection, wherein the broad reactivity of the anti-CD3 with all T cells results in modulation of the entire T cell population. The therapeutic methods of the present invention result in modulation of only the particular T cell subset expressing the TCR V region subfamily of interest.

In addition, reagents directed to TCR Vβ3 region subfamilies, as disclosed herein, are applicable to the treatment of groups of patients showing similar V region expression. This contrasts with therapy directed to a unique clonal Vβ3 (V-D-J-C) chain which should be useful only in those individual patients in which that precise TCR Vβ3 chain is expressed.

Second generation anti-TCR Vβ3 antibody-based therapeutics are expected to rely on further refinements of our knowledge of the association of particular V, D, and J regions of β TCR genes with specific disease states. For example, patients may be further subdivided into groups for treatment based upon the Vβ3 TCR V, D and J regions involved. The objective remains the modulation of only the disease-related T cells, while sparing or not affecting other T cells in the subject to achieve a greater specificity of therapy.

According to the present invention, where Vβ3 is discussed above, it refers to any member of the Vβ3 family; preferably the subfamily is Vβ3.1.

5.6. PHARMACEUTICAL COMPOSITIONS OF THE INVENTION

The preclinical and clinical therapeutic use of the present invention in the treatment of immune-related diseases or disorders will be best accomplished by those of skill, employing accepted principles of diagnosis and treatment. Such principles are known in the art, and are set forth, for example, in Braunwald, E. et al., eds., *Harrison's Principles of Internal Medicine*, 11th Ed., McGraw-Hill, publisher, New York, N.Y. (1987).

The antibodies, fragments and derivatives of the present invention, are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intradermal, intramuscular, intraperitoneal, transdermal, or buccal routes. Alternatively, or concurrently, administration may be by the oral route. The pharmaceutical compositions can be administered parenterally by bolus injection or by gradual perfusion over time.

The dosage administered will be dependent upon the age, sex, health, and weight of the recipient, kind of concurrent treatment, if any, frequency of treatment, and the nature of the effect desired. The dose ranges for the administration of the compositions of the present invention are those large enough to produce the desired effect. The doses should not be so large as to cause adverse side effects, such as unwanted cross reactions, generalized immunosuppression, anaphylactic reactions and the like.

Preferred doses for humans range between about 0.0001–25 mg of antibody, fragment or derivative per kg body weight.

In addition to antibody, fragment, or derivative of the invention which is itself pharmacologically active, pharmaceutical compositions preferably contain suitable pharmaceutically acceptable carriers comprising excipients and auxiliaries which facilitate processing of the active compounds into preparations which can be used pharmaceutically. Such pharmaceutically acceptable carrier are sterile. Moreover, as used herein, the term pharmaceutically acceptable carriers does not include cell culture media, or any components not approved for use in humans.

Suitable formulations for parenteral administration include aqueous solutions of the antibody in water-soluble form, for example, water-soluble salts. In addition, suspensions of the antibody as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. The antibodies, fragments or derivatives of the invention are preferably formulated in purified form substantially free of aggregates and other protein materials, preferably at concentrations of about 1.0 ng/ml to 100 mg/ml.

The compositions are formulated using conventional pharmaceutically acceptable parenteral vehicles for administration by injection. These vehicles are nontoxic and therapeutic, and a number of formulations are set forth in *Remington's Pharmaceutical Sciences*, 16th ed., Mack Publishing Co., Easton, Pa. (1980). Non-limiting examples of excipients are water, saline, Ringer's solution, dextrose solution and Hank's balanced salt solution. Formulations according to the invention may also contain minor amounts of additives such as substances that maintain isotonicity, physiological Ph, and stability.

To enhance delivery or bioactivity, the antibodies, fragment or derivative thereof, can be incorporated into liposomes using methods and compounds known in the art.

Having now generally described the invention, the same will be more readily understood through reference to the following examples which are provided by way of illustration, and are not intended to be limiting of the present invention, unless specified.

EXAMPLE 6

PRODUCTION AND CHARACTERIZATION OF MONOCLONAL ANTIBODIES TO Vβ3.1

6.1. METHODS

6.1.1. IMMUNIZATION AND SCREENING FOR HYBRIDOMAS

Soluble purified Vβ3.1 protein (20 µg) was obtained as described in Section 6.1.7. and emulsified in complete Freund's adjuvant before injection intraperitoneally (i.p.) and subcutaneously (s.c.) into Balb/c mice. At 3–4 week intervals, the mice were immunized i.p. with 20 µg Vβ3.1 emulsified in Freund's adjuvant. Four weeks after the third immunization, one mouse was boosted intravenously (i.v.) with 20 µg Vβ3.1 and the spleen removed 4 days later. Splenocytes were fused with P3X63-Ag8.653 myeloma cells by addition of 1 ml 50% (w/v) PEG-1500 (Boehringer Mannheim, Indianapolis Ind.), then diluted with 20 ml serum-free Opti-MEM medium (GIBCO). After fusion, the cells were plated into wells of 96-well flat-bottomed plates and selected in Opti-MEM-I medium containing 7.5% FCS, 10% calf serum (Hyclone), 5% Origen (IGEN, Rockville, Md.) and HAT (GIBCO). Wells with growth were screened for the production of anti-TCR mAbs using a "TCR capture" screening ELISA.

Wells of flat bottomed 96 well plates were coated overnight at 4° C. with 100 µl of goat anti-mouse IgG Fc-specific antibodies (Cappel, Westchester, Pa.) at 2 µg/ml in PBS. After blocking plates for 1 hr with a solution of 1% BSA in PBS, plates were washed with wash buffer (0.05% Tween-20 in PBS). Hybridoma culture supernatant (100 µl) was added and incubated for 1–2 hrs at room temperature. The wells were then washed with wash buffer, and 100 µl of a solution containing approximately 1 µg/ml soluble Vβ3.1, horseradish peroxidase-conjugated W76-Fab fragment (an antibody which reacts with Cβ regions), 2% normal mouse serum, 0.25% NP-40, and 25% FCS in wash buffer was added and incubated for 2 hr. After washing, the reactions were developed. Isotype analysis was done using a commercial kit (Boehringer Mannheim).

6.1.2. RADIOLABELING AND IMMUNOPRECIPITATION

Surface proteins were radiolabeled with $^{125}$I by the lactoperoxidase technique. Briefly, $5 \times 10^7$ cells were washed 3 times with PBS and incubated 30 minutes at room temperature in 1 ml PBS with 100 ng lactoperoxidase, 2 ng glucose oxidase, 1 mCi Na$^{125}$I and 10 mM glucose. The cells were washed twice in PBS with 10 mM NaI and lysed for 1 hour at 4° C. in 1.0 ml of a solution containing 10 mM Tris-HCl, pH 8.0, 0.15M NaCl, 1% NP-40, 1 mM PMSF, 0.6 U/ml aprotinin, 1 mM EDTA, and 10 mM iodoacetamide. Nuclei from lysed cells were pelleted and discarded. Hemoglobin was added to a final concentration of 0.5% and the lysate was then purified on a NAP-5 Sephadex G25 column (Pharmacia) to remove free $^{125}$I.

Prior to immunoprecipitation, the lysate was precleared by incubation with 0.2 ml Pansorbin (Calbiochem, La Jolla, Calif.) per ml lysate for 1 hour at 4° C. Control mAbs or 50 µl of mAb culture supernatant was added to $2 \times 10^6$ cpm of lysate and incubated overnight at 4° C. Immune complexes were precipitated by addition of 5–10 µg goat anti-mouse IgG-Sepharose (Cappel) and incubated 4 hrs at 4° C. After washing 4 times in lysis buffer, the immunoprecipitates were eluted from the Sepharose by boiling for 5 min in SDS-PAGE sample buffer and analyzed under reducing conditions on an 11% SDS polyacrylamide gel. The gel was dried under vacuum and analyzed via autoradiography.

6.1.3. FLOW CYTOMETRY METHODS

For single color immunofluorescence, $5 \times 10^5$ cells were incubated with hybridoma supernatants or control mAbs for 30 minutes on ice. The cells were then pelleted, washed twice with flow cytometry buffer (PBS with 0.02% NaN$_3$ and 2% FCS) and incubated with fluorescein-conjugated goat anti-mouse IgG F(ab)'$_2$ (Cappel) for 30 minutes on ice. When the hamster mAb 2C11 was tested, a fluorescein-conjugated rabbit anti-hamster IgG F(ab)'$_2$ (Jackson ImmunoResearch, West Grove, Pa.) was the detecting reagent. After 2 washes with flow cytometry buffer, the cells were resuspended in 1.5 ml flow cytometry buffer and analyzed on a FACScan cytofluorograph (Becton Dickinson, Mountain View, Calif.). For two color immunofluorescence, 100 µl heparinized or EDTA-treated whole blood from normal human donors was incubated with hybridoma supernatants or control mAbs for 30 minutes on ice. The cells were then pelleted, washed twice with flow cytometry buffer and incubated with fluorescein-conjugated goat anti-mouse IgG F(ab)'$_2$ (Cappel) for 30 minutes on ice. After 1 wash with flow cytometry buffer, the cells were incubated with phycoerythrin-conjugated mAb specific for CD4, CD8 or CD3 for 30 min. Erythrocytes were then lysed by incubating 5 min with 2 ml of lysing solution (0.16M NH$_4$Cl, 0.01M KHCO$_3$, 0.1 mM EDTA) at ambient temperature. The remaining cells were pelleted, washed once with flow cytometry buffer and resuspended in 0.5 ml flow cytometry buffer. Flow cytometry analysis was performed after gating on the lymphocyte population.

6.1.4. STIMULATION OF T CELL PROLIFERATION USING ANTI-TCR MABS

Heparinized blood from normal human donors was diluted 2-fold with PBS, and mononuclear cells were isolated by centrifugation on Ficoll-Hypaque (Pharmacia, Piscataway, N.J.). After washing 2–3 times with PBS to remove platelets, the cells were resuspended at $1 \times 10^6$ cells/ml in RPMI-1640 medium supplemented with 10% normal human serum and cultured on mAb-coated plates prepared as follows. Wells of 24-well plates were incubated overnight at 4° C. with goat anti-mouse IgG-Fc specific antibody (Cappel) diluted to 1 µg/ml in PBS. After 1 wash with PBS, 100 ml of one of the anti-Vβ3 (5E4 or 8F10) culture supernatants was added and incubated 1 hour at 37° C. After the plates were washed several times with RPMI-1640, cells were added and cultured for 48 hr at 37° C. in a 5% CO$_2$ atmosphere. Recombinant IL-2 (Amgen, Thousand Oaks, Calif.) diluted to 20 U/mi in medium lacking mAbs was then added at 3–5 day intervals. After 7 days the cells were restimulated by incubating on mAb-coated plates. Cells were analyzed by flow cytometry cytometry and harvested for RNA preparation 5–7 days after the last stimulation.

6.1.5. PCR ANALYSIS OF Vβ3 MAB-STIMULATED PBL

Total RNA was prepared by the acid-phenolguanidinium thiocyanate technique Clontech Laboratories, Palo Alto, Calif.). cDNA was synthesized from 1 µg of RNA using the Geneamp® RNA PCR kit (Perkin Elmer Cetus, Norwalk, Conn.) and oligo dT for priming. PCR was performed using a sense Vβ3-specific primer (3-1 primer 5'GGAGATATTCCTGAGGGGTAC3'SEQ ID NO:1 or 3-2 primer 5'GATGTGAAAGTAACCCAGAGC3'SEQ ID NO:2) and an antisense Cβ primer (5'CTGATGGCTCAAACACAGCGACCTCG3'SEQ ID NO:3) using 0.5 μM of each primer, 2.5 U AmpliTaq DNA polymerase (Perkin Elmer Cetus), 50 mM KCl, 10 mM Tris-HCl, pH 8.3, 2 mM $MgCl_2$ and 0.2 mM of each deoxynucleoside triphosphate.

The PCR profile used for the amplifications with the 3-1 primer was: denaturation at 94° C. for 1 min, annealing at 60° C. for 2 min, and extension at 72° C. for 2 min for 25 cycles. When the 3-2 primer was used, PCR conditions were the same except that annealing was done at 56° C. After amplification, the reaction was made 5 mM in $MgCl_2$ and PCR products were blunt-ended by incubating 30 min at room temperature with 1-2 U Klenow fragment. Half of the PCR product was purified from a 1% low melting point agarose gel, phosphorylated with T4 DNA kinase as described and cloned into SmaI-digested, pUC18 which had been treated with calf intestinal phosphatase (Boehringer Mannheim, Indianapolis, Ind.). This DNA was used to transform DH5α competent cells and individual colonies were isolated and plasmid DNA was sequenced with T7 DNA polymerase (Sequenase, U.S. Biochemical, Cleveland, Ohio).

FLOW CYTOMETRY METHODS USING MONKEY CELLS

For two color immunofluorescence, 100 μl heparinized or EDTA-treated whole blood from cynomolgous macaques (TSI Mason, Research) was incubated with FITC-labelled 8F10 and 5E4 and with a mixture of phycoerythrin-conjugated mAb specific for CD4 and CD8 for 30 minutes. Erythrocytes were then lysed by incubating 5 minutes with 2 ml of lysing solution (0.16M $NH_4Cl$, 0.01M $KHCO_3$, 0.1 mM EDTA) at ambient temperature. The remaining cells were pelleted, washed once with flow cytometry buffer and resuspended in 0.5 ml flow cytometry buffer. Flow cytometry analysis was performed after gating on the lymphocyte population.

6.1.7. PRODUCTION OF SOLUBLE Vβ3.1 PROTEIN (SVβ3.1)

The 1.3 kilobase β-chain insert of YT35 (Yanagi et al., 1984, Nature 308:148-149) was subcloned into pUC18, digested with StuI and SphI, and the large fragment containing the vector and most of the β-chain coding region was purified. This large fragment was then ligated to two complementary oligomers (5'CCTGGGGTAGAGCAGACTGTTCGTAGCATG 3'SEQ ID NO:4 and 5'CTACGAACAGTCTGCTCTAC-CCCAGG 3'SEQ ID NO:5, New England Biolabs, Beverley, Mass.) which had been annealed by incubating at 65° C. for 15 minutes and then slowly cooled to room temperature. This yielded a human TCR β-chain construct designated sVβ8.1, similar to the previously described murine soluble construct (Gascoigne, et al., 1990, J. Biol. Chem., 265:9296-9301) with a glycine to serine substitution at amino acid 258 after the initiation codon followed by an in-frame stop codon.

The cDNA clone PL4.4 (Concannon, et al., 1986, Proc. Natl. Acad. Sci. USA, 83: 6598-6602) was used as a template for the Vβ3.1 coding sequence. Since this clone lacked DNA encoding a full-length signal or leader sequence, the DNA encoding the leader sequence from the cDNA clone YT35 was joined to the DNA encoding the V, D and J regions of PL4.4 using site-directed mutagenesis. The TCR coding region of YT35 (Vβ8.1, Cβ1) was cloned into pUC18 and digested with HincII and BglII. The large fragment, encompassing pUC18, the entire TCR leader (L) and V regions, and the Cβ1 region 3' of the BglII site, was ligated to a StuI/BglII fragment from the clone PL4.4 (Vβ3.1, Cβ2), encompassing the entire V, D, and J regions of PL4.4 and the Cβ2 region 5' of the BglII site. The BglII site is common to both the Cβ1 and Cβ2 sequences. This cloning intermediate contained the entire V, D, J and C region of PL4.4 properly fused with the Cβ1 of YT35 at the 3' end, but out of frame with Vβ8.1 of YT35 at the 5' end. Site-directed mutagenesis with the oligomer 5' GCATACA-GATGCTAAAGTAACCCAGAGAG 3'SEQ ID NO:6 was used to loop out the unwanted Vβ8.1 sequence and restore the open reading frame. The first 13 nucleotides of this oligomer hybridizes to DNA encoding the Vβ8.1 L region up to the L-Vβ8.1 junction while the remainder of the oligomer binds to the N-terminal coding region of Vβ3.1. Hybridization of this oligomer to the intermediate caused the intervening unwanted Vβ8 sequence to be "looped out". Briefly, the Vβ3.1 intermediate DNA (1 μg) was linearized with XmnI (this enzyme cuts in the ampicillin resistance gene of pUC18), dephosphorylated with calf intestinal phosphatase (Boehringer Mannheim), and mixed with 1 μg of EcoRI/HindIII digested and dephosphorylated pUC18 in a final volume of 25 μl. The DNA mixture was denatured by incubating 5 minutes with 25 μl 0.4M NaOH, neutralized by the addition of 450 μl of 0.1M Tris-HCl, pH7.5 and then heated at 68° C. for 2 hours. This created a small proportion of heteroduplex DNA consisting of one strand of pUC18 only and one strand of pUC18 plus Vβ3.1 intermediate DNA. The mutagenic oligomer (50 pmoles) was phosphorylated, annealed to 45 μl of heteroduplex DNA for 20 minutes at 60° C. and cooled at room temperature for 10 minutes. The gap was filled and the plasmid closed by the addition of 10 mM deoxynucleotides, 5 U of the Klenow fragment of E. coli DNA polymerase I, 4 mM dithiothreitol, 0.2 mM adenosine triphosphate, and 100 U T4 DNA ligase (all enzymes were purchased from New England Biolabs, Beverly, Mass.). Dilutions of the ligation mixture were used to transform DH5α competent cells (BRL). Ampicillin resistant colonies were transferred to nylon membranes (Colony/Plaque Screen, New England Nuclear, Boston, Mass.) and those harboring the mutation were detected by colony hybridization with the 5'-end labeled ($\gamma^{32}$P-ATP, New England Nuclear) mutagenic oligomer. Hybridization was performed at 37° C. in 0.9M NaCl, 1.0M sodium citrate. Filters were washed at 65° C., a temperature which favors hybridization of the oligomer to correctly mutagenized DNA. DNA from positive colonies was analyzed by restriction digestion and DNA sequencing to confirm that it encoded a full-length Vβ3.1 chain. This construct was designated flVβ3.1.

To generate sVβ3.1, the small EcoRI/BglII fragment from flVβ3.1 was ligated to the large EcoRI/BglII fragment from sVβ8.1. This ligated fragment was then cloned into the XhoI site of the mammalian expression vector pTCSgpt (see Intl. Patent Publ. #WO 91/05047, published Apr. 18, 1991) to generate sVβ3.1-pTCSgpt.

Calcium phosphate-mediated cotransfection of CHO DUX B11 cells was performed using 3 μg pSV2 DHFR and 30 μg sVβ3-pTCSgpt as described (Graham and van der Erb, 1973, Virol. 52:456-467). Cells were selected by growth in media containing methotrexate (Lederle, White Plains, N.Y.) as described (Kaufman, et al., 1985, Molec. and Cell. Biol. 5:1750-1759). Subclones were analyzed for TCR β-chain production with a dual mAb sandwich ELISA specific for TCR β-chain in which lysates of the TCR-positive cell line Jurkat served as standards. Briefly, 96 well flat-bottomed plates (Immulon 2, Dynatech Laboratories, Chantilly, Va.) were coated overnight at room temperature in a humidified chamber with 100 µl anti-TCR Cβ mAb W76 at 2 µg/ml in PBS. After incubating the plates for 2 hours at 37° C. in blocking buffer (1% BSA, 0.05% Tween-20, 0.15M NaCl, 0.025M Tris-HCl, pH 7.4, 0.01% thimerosal), the samples to be tested or Jurkat lysate standards were diluted in blocking buffer containing 0.25% NP-40 and the plates were incubated 1.5 hours at 37° C. The plates were washed 3 times with wash buffer (0.05% Tween-20, 0.01% thimerosal in PBS) and 100 µl of horseradish peroxidase-conjugated βF1 diluted in blocking buffer containing 50% FCS was added and allowed to incubate 1.5 hours at 37° C. After 3 washes, the plates were developed using 100 µl substrate solution (0.2% o-phenylenediamine, 0.017M sodium citrate, 0.065M $Na_2HPO_4$, 0.04% $H_2O_2$). This reaction was stopped by addition of 50 µl 2N $H_2SO_4$ and the absorbance of each well was read at 490 nm on a microtiter plate reader (Dynatech). Positive subclones from the cotransfection were identified using the ELISA described above and were subsequently amplified by culturing the cells in increasing concentrations of methotrexate (Kaufman, et al., Molec. Cell. Biol., 5:1750–1759). A subclone cultured in 250 Nm methotrexate was selected for further study and designated CHO-sVβ3.1.

For large-scale culture, the CHO-sVβ3.1 cells were grown on microcarriers (Ventregel II, Ventrex Laboratories, Inc., Portland, Me.) in CHO-SFM media (Gibco) containing 1% dialyzed FCS (Gibco). The supernatant from 6 liters of culture was harvested at confluence, concentrated 30-fold by ultrafiltration (Benchmark Vortex Flow cytometry System, Membrex, Inc. Fairfield, N.J.) and the sVβ3.1 protein was purified by affinity chromatography on a column of the anti-TCR β chain mAb W76 coupled to Affigel-10 (Bio-Rad, Richmond, Calif.). The column was eluted with 50 mM diethylamine, Ph 11.5 and fractions were neutralized with 1/10th volume 0.5M HEPES, pH 7.0. Protein concentration was estimated using the BCA protein reagent assay (Pierce, Rockford, Ill.) versus a BSA standard curve and purity was assessed by Coomassie Blue and silver staining of material run on SDS-PAGE.

6.1.8. MURINE T CELL EXPRESSING HUMAN VB3.1

To create a T cell line expressing human Vβ3, GLS5hβ⁻ murine T hybridoma cells were transfected by electroporation with the full-length Vβ3.1 insert from flVβ3.1 that had been cloned into the BamH1 site of the mammalian expression vector pFneo (Ohashi et al., 1985, Nature 316:606–607). Five million (5×10⁶) GLS5hβ⁻ cells suspended in 0.8 ml Opti-MEM-I medium (Gibco) were mixed with 20 µg plasmid DNA and subjected to 200 volts, 960 µF using a Genepulser electroporation apparatus (BioRad). After 2 days of culture, the cells were resuspended in media containing 1 mg/ml G-418 (Gibco). After approximately 2 weeks, the cultures were analyzed for TCR expression by flow cytometry cytometry with anti-murine CD3 Mab 2C11. Limiting dilution cloning yielded subclones which were chosen on the basis of positive reactivity with 2C11 and negative reactivity with H57-597, a Mab specific for the murine TCR β-chain. A positive subclone was designated GLS5hβ⁻/hVβ3.1.

6.2. RESULTS

One fusion as described above resulted in 6 Mabs which were strongly reactive with Vβ3 in the TCR capture screening ELISA. Two of these, designated 5E4 and 8F10, were also reactive with normal human PBL (see below) by flow cytometry cytometry and were selected for further analysis. Both Mabs were of the IgG1 isotype. To confirm that 5E4 and 8F10 recognized cell-surface TCR β chains, the mAbs were tested for their ability to bind to the surface of a murine T cell hybridoma expressing human Vβ3.1. The results appear in FIGS. 1A–1F. Both mAbs reacted with the murine transfectant, although 5E4 exhibited weaker fluorescence intensity than either 8F10 or the positive control mAb specific for murine CD3, 2C11. None of these mAbs reacted with the TCR-negative mutant cell line.

Experiments were then performed to determine the biochemical characteristics of the molecule recognized by 5E4 and 8F10. Each mAb was used to immunoprecipitate $^{125}I$-labeled surface proteins from the murine T cell transfectant. The immunoprecipitates were subjected to SDS-PAGE under reducing conditions and the gels were analyzed by autoradiography (FIG. 2). Both 5E4 and 8F10 mAbs immunoprecipitated a molecule of identical size to that immunoprecipitated by mAb βF1, a TCR Cβ specific antibody, indicating that the new mAbs bound to a TCR-like molecule. As expected, a mAb specific for the constant region of the human TCR α chain, αF1, did not react with the murine α chain expressed by the transfectant and so served as a negative control.

PBL from several normal human donors were analyzed for reactivity with 5E4 and 8F10. To delineate which T cell population was stained, the samples were also reacted with phycoerythrin conjugates of either Leu-4 (anti-CD3) or with a mixture of Leu-3a (anti-CD4) and Leu-2a (anti-CD8) mAbs. FIGS. 3A-1, 3A-2, and 3A-3 shows representative results obtained from one donor. Analysis of reactivity with PBL from 19 donors showed that 5E4 reacted with 0.7–8.1% (mean=4.0%) of peripheral blood T cells. 8F10 reacted with 0.9–9.9% (mean=4.9%) of peripheral blood T cells. These results indicate that individuals vary considerably in expression of the Vβ3 epitope or epitopes recognized by 5E4 and 8F10.

Family studies in humans using the available anti-TCR V region antibodies have recently demonstrated an influence of MHC on TCR α and β chain expression as, MHC-identical individuals appeared to have a more similar pattern of V region usage than did MHC-mismatched siblings. The discovery of the mAbs of the present invention will facilitate study of the relationship between MHC and Vβ3 expression.

Figures 3, 3A:
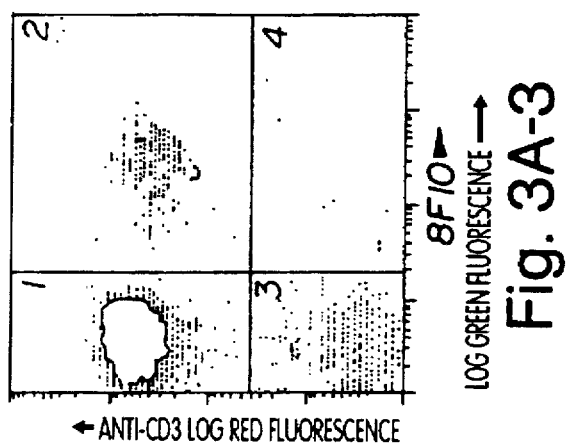
Figures 2, 3A:
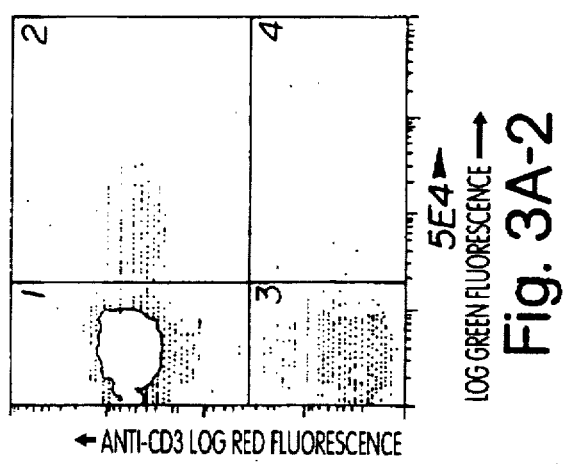
Figures 1, 3A:
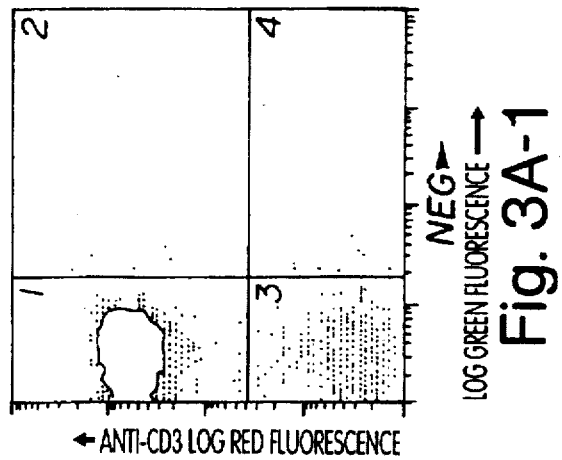
Figures 2, 3B:
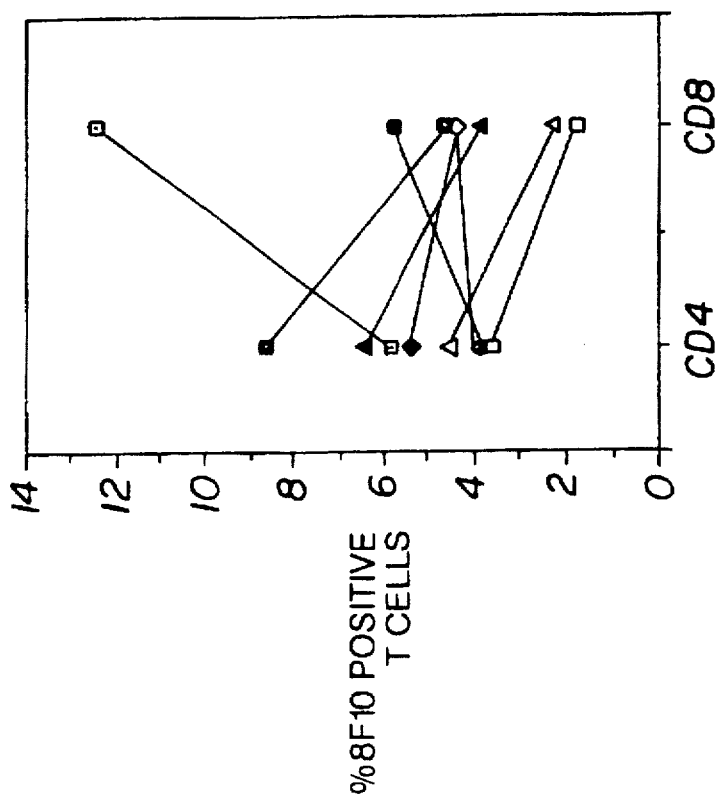
Figures 1, 3B:
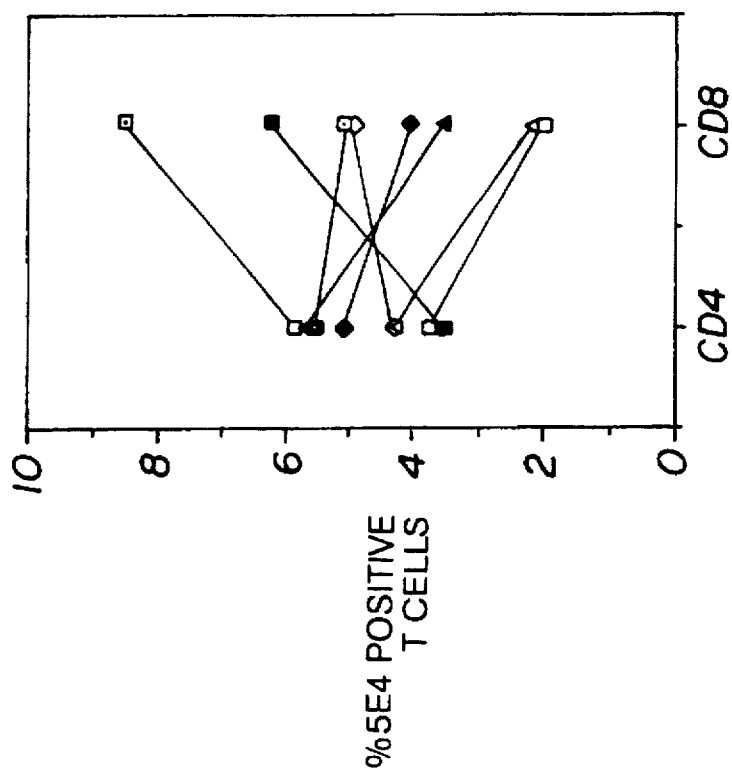
Figures 3, 5:
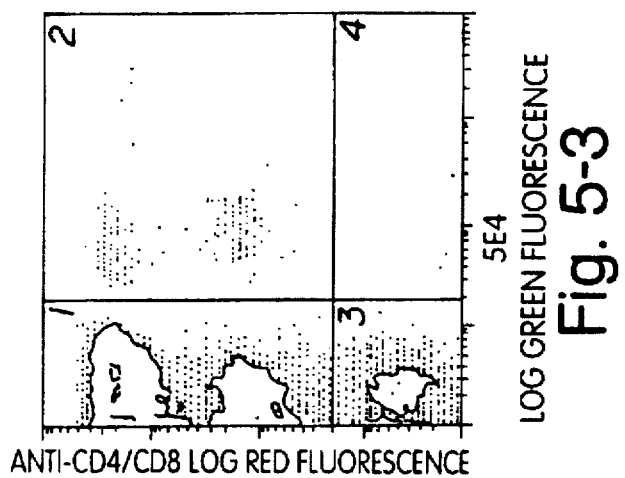
Figures 2, 5:
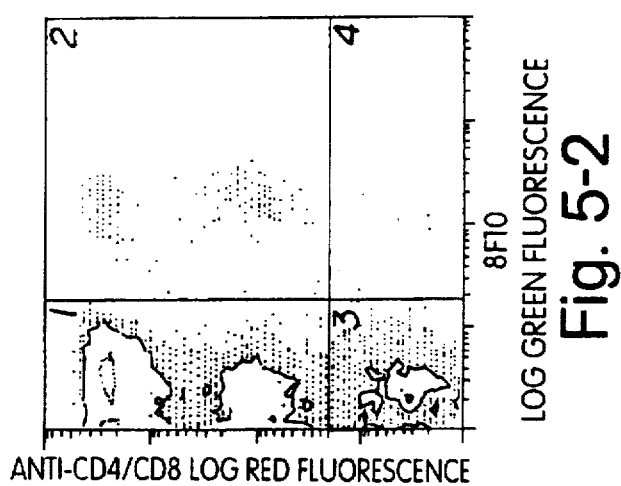
Figures 1, 5:
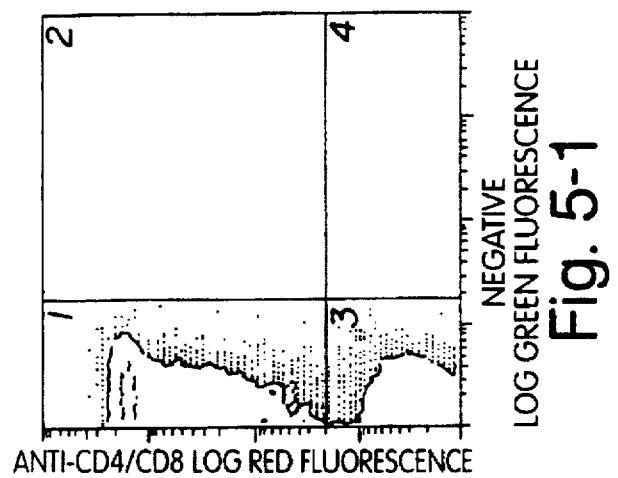

To determine whether Vβ3.1 was preferentially expressed in CD4+ or CD8+ T cells, PBL from 5 donors having 5E4 or 8F10 reactive cells were analyzed by 2-color immunofluorescence for reactivity with either anti-CD4 or anti-CD8 mAbs (FIGS. 3B-1 and 3B-2). PBL from 2 donors exhibited much higher 5E4 and 8F10 reactivity in the CD8-reactive T cells (closed squares) as compared to the CD4 reactive T cells (open squares). PBL from a different donor showed higher 8F10 reactivity in the CD4⁺ population. Thus, though certain individuals exhibited an uneven distribution among CD4 and CD8 positive T cells of the Vβ3.1 epitopes detected by the new mAbs, there was no apparent bias toward either population in the limited sample presented here.

The skewing of Vβ3 expression to either CD8⁺ or CD4⁺ T cells observed in individuals could reflect the influences of different Class I or Class II MHC gene products on selection of Vβ3 cells. However, the contribution of antigenic influences to Vβ3 expression cannot be ruled out, since Vβ3 expression in an antigenically "naive" populations, such as cord blood lymphocytes, has not been studied.

To study the fine specificity of the 5E4 and 8F10 mAbs, the mAbs were used to stimulate proliferation of human PBL cell lines, which were then subjected to PCR analysis of expressed Vβ3 sequences using Cβ- and Vβ3.1-specific primers. Ficoll-Hypaque purified PBMC from 2 donors were stimulated with either 5E4 or 8F10. After approximately 2.5 weeks of culture, the cells were harvested for flow cytometry cytometric analysis with the mAbs and for RNA preparation.

In two 5E4-stimulated lines, approximately 70% of the cells stained with 5E4. In the two 8F10-stimulated lines, approximately 83% of the cells were reactive with 8F10. Lines derived by stimulating with either mAb were equally reactive with the other mAb, suggesting that the two mAbs recognize nearly identical cell populations though not necessarily the same epitope.

To determine if these antibody-stimulated cell lines expressed Vβ3 subfamily genes distinct from Vβ3.1, RNA from the 4 PBL lines described above was reverse transcribed using an oligo dT primer and subjected to PCR analysis with a Cβ primer and the 3-2 primer (which can detect Vβ3.1 and a published Vβ3.2 sequences). The PCR products were then cloned and sequenced. A total of 6 sequences from individual bacterial colonies were obtained for each mAb-stimulated T cell group (4 from 5E4-stimulated cells of donor 1, 2 from 5E4-stimulated cell from donor 2, and 3 each from 8F10-stimulated cells from both donors). All 12 sequences were identical to the Vβ3.1 sequence of clone PL4.4, with one exception: one sequence from the donor 1 5E4-stimulated line contained a single nucleotide change at base pair #118 in the PL4.4 sequence, T→C. This nucleotide change could simply represent a PCR artifact or could result from an allelic difference in Vβ3.1. Since no Vβ3.2 sequences were found, it is likely that 5E4 and 8F10 reactivity is restricted to cells expressing genes of the Vβ3.1 subfamily.

Cloning and sequencing of PCR products was performed to detect any restriction in D or J segment usage in the Vβ3.1 sequences expressed by the above mAb-stimulated cells. The PCR analysis was performed as above using the 3-2 V region primer (hybridizing about 100 b.p. upstream from the V-D-J junction of clone PL4.4) and the Cβ primer in order to generate short fragments which could be completely sequenced with relative ease. Vβ3 sequences of 5E4- and 8F10-stimulated PBL from only one donor were analyzed. Fourteen independent DNA sequences from this analysis (8 from the 5E4-stimulated line and 6 from the 8F10-stimulated line) are shown in FIG. 4 which also shows the V-D-J junction of PL4.4 (the cDNA encoding the Vβ3.1 protein used as immunogen for the new mAbs). There were no discernible differences in the specificity of the two mAbs (5E4 and 8F10) in that sequences from the cell lines derived using either mAb exhibited a comparable degree of variability in J region usage.

Of note is that 9 (5 of the 5E4-stimulated type and 4 of the 8F10-stimulated type) of the 14 Vβ3.1 clones represented here utilize the Jβ2.7 gene segment. Also, 12/14 rearranged to the Cβ2 gene segment. The Jβ2.7 gene was frequently utilized by both the 5E4- and 8F10-stimulated PBL. Despite the apparent preferential usage of Jβ2.7 in the Vβ3.1 sequences of 5E4- and 8F10-stimulated PBL, other J gene segments were also used, albeit at a much lower frequencies. While it is possible that the epitope(s) recognized by the two mAbs is formed by shared regions of identity or homology among the various Jβ subfamilies, the variety of J regions observed suggests that the mAbs are not J region-specific.

It is possible that rearrangements involving the Vβ3.1 gene preferentially utilize the Jβ2.7 gene. Some J segments have been reported to be utilized more frequently though not in association with a particular V gene segment.

In conclusion, PCR analysis of mAb-stimulated human PBL showed that 5E4 and 8F10 were specific for Vβ3.1-encoded TCR β chains.

The mAbs 5E4 and 8F10 are therefore useful for confirming these observations and for further analysis and modulation of Vβ3 cells in normal and disease conditions.

PBL from 3 cynomolgous macaques were analyzed for reactivity with 5E4 and 8F10. To delineate which T cell population was stained, the samples were also reacted with phycoerythrin conjugates of a mixture of Leu-3a (anti-CD4) and Leu-2a (anti-CD8) mAbs, both of which have cross reactivity with macaque PBL. FIGS. 5-1, 5-2, and 5-3 shows representative results obtained from cynomolgous macaque showing that 5E4 reacted with 0.2 to 1.46% (mean=0.83%) of peripheral blood $CD4^+/CD8^+$ T cells. 8F10 reacted with 0.6–1.40% (mean=1.07%) of macaque peripheral blood T cells. These results indicate that the mAbs of the present invention cross react with cynomolgous macaque peripheral blood T cells.

7. EXAMPLE

MONOCLONAL ANTIBODIES REACTIVE WITH THE VARIABLE REGIONS OF α, β HUMAN T CELL ANTIGEN RECEPTOR ARE USEFUL IN THE TREATMENT OF RHEUMATOID ARTHRITIS

The first step needed in the development of T cell receptor specific therapeutics is to correlate specific T cell receptor gene usage with disease. Once it is known which T cell receptors (TCRs) are primarily involved in the disease, specific therapeutics can be produced.

A panel of TCR variable region genes was used to determine which variable regions correlate with rheumatoid arthritis. The data presented infra involves the analysis of rheumatoid arthritis patient samples using Vα and Vβ TCR gene probes. Similar analysis could also be done using Vγ and Vδ genes as well.

7.1. MATERIALS AND METHODS

SAMPLES: Paired synovial membrane derived T cell lines and peripheral blood T cell lines were prepared from 12 patients with RA. Peripheral blood lines were also obtained from 5 normal individuals for controls using cell culture procedures.

T CELL RECEPTOR VARIABLE REGION GENE PROBES There are 17 human Vα and 24 human Vβ subfamilies that have been identified to date (Robinson, M. A., 1991 J. Immunol. 146 4392–4397). These Vβ subfamilies are named Vβ1 to Vβ24. As additional variable regions become available, they may similarly be tested. Once correlations between disease and specific TCR V subfamilies have been identified, the specific member of the subfamily responsible for the correlation can also be identified.

RNA PREPARATIONS

RNA was isolated by the guanidinium isothiocyanate cesium chloride procedure (Maniatis, T., et al., 1982, In "Molecular Cloning: A Laboratory Manual", Cold Spring Harbor Laboratories, N.Y.). Total RNA was precipitated twice in 0.3M sodium acetate and 2.5 volumes of ethanol. On average, 5 to 10 μg of total RNA was obtained from 10 million cultured T cells.

T CELL ANTIGEN RECEPTOR USAGE ANALYSIS

The usage of T cell antigen receptor α and β chains in the T cell lines was determined using 3 major steps: i) cDNA synthesis; ii) polymerase chain reaction amplification; and iii) DNA slot blot analysis.

cDNA SYNTHESIS

Five μg of total RNA from each sample was primed for cDNA synthesis using Cα and Cβ oligonucleotides. To analyze TCR γ,δ gene usage, Cγ and Cδ primers could be used in an analogous fashion. Both Cα and Cβ primers were 18-mers synthesized by New England Biolabs, Beverly, Mass. using the published sequences of the α and β constant regions (Yanagi, Y., et al., 1984, Nature, 308, 145–149). The sequence of the Cα primer (5'-TTAGAGTCTCTCAGCTGG-3'SEQ ID NO:7) is located 31 nucleotides 3' from the $NH_2$ terminus of the α chain constant region. The sequence for the Cβ primer (5'-TTCTGATGGCTCAAACAC-3'SEQ ID NO:8) is located 36 nucleotides 3' from the $NH_2$ terminus of the β chain constant region. The Cβ oligonucleotide primed cDNA synthesis from both β chain constant regions (Yanagi, Y., et al., 1984, Nature, 308, 145–149; Jones, N., et al., 1984, Nature, 227, 311–314). The location of these primers was chosen such that the synthesized CDNA would comprise the variable, diversity, and joining regions of the T cell receptor MRNA and only a small portion of the constant region.

First strand DNA synthesis was performed according to published procedures (Okayama, H. and Berg, P., 1982, Mol. Cell. Biol., 2, 161–170; Gubler, U. and Hoffman, B.J., 1983, Gene, 25, 263–269) except that the reaction was terminated prior to synthesis of the second strand. The resulting templates were in the form of RNA:DNA hybrids. These duplexes were then used in an oligo-dG tailing reaction (Deng, G-R. and Wu, R., 1983, Meth. in Enzymol., 100, 96–117) which preferentially tails the 3' end of the CDNA strand over the RNA strand.

POLYMERASE CHAIN REACTION (PCR) AMPLIFICATION The PCR reaction was performed in a thermocycler (Perkin-Elmer, Norwalk, Conn.) using recombinant Taq DNA polymerase (Cetus Corp., Emeryville, Calif.). Oligonucleotides, $d(C)_{10}$, and Cα and Cβ, were used as primers for amplification. The PCR amplification procedure of Loh, E. Y., et al. (1989, Nature, 243, 217–243) was used with the following modifications. PCR amplification was done for 30 cycles with each cycle comprising incubations at 92° C. for 1 minute, 50° C. for 1.5 minutes and 72° C. for 2.5 minutes. The last extension reaction was for 10 minutes at 72° C. All samples were amplified a total of 3 times with isolation of the amplified DNA fragment of about 300–400 base pairs between each round. The final amplified DNA samples were then precipitated with spermine to remove free nucleotides, before labeling with $^{32}p$ radiolabeled nucleotides. Labeling was done during 5 cycles of PCR amplification using all four $^{32}p$ labeled nucleotides at a ratio of 1:10 non-radiolabeled nucleotides. The resulting $^{32}p$ labeled DNAs were purified on elute-tip™ columns (Schleicher & Schuell, Keene, N.H.) to remove non-incorporated $^{32}P$ nucleotides.

DNA SLOT BLOT ANALYSIS

DNA slot blots were prepared using a slot blot apparatus (Schleicher & Schuell, Keene, N.H.) and nylon membranes (Oncor, Gaithersburg, Md.) according to manufacturer's protocols. A panel of cDNA subclones comprising the variable region of α and β chain TCR genes was spotted in duplicate on each slot blot (3 μg per slot). After the blots had been prepared containing the panel of TCR V region DNAs, individual blots were then hybridized to the $^{32}P$ labeled T cell derived cDNA generated in step #2. Individual patient samples were hybridized to duplicate blots. Hybridization condition and washes (Southern, E., 1979, J. Mol. Biol., 98, 503–517) were chosen to ensure no cross-hybridization between members of different subfamilies. The wash steps were performed at 42° C. in 0.2×SSC (30 mM sodium chloride, 3 Mm sodium citrate, pH 7.4) with 0.1% sodium dodecyl sulfate using 4 washes of 20 minutes each. Following washing, the blots were blotted dry, and then autoradiographed at −70° C. for 2–6 days using Eastman Kodak, X-Omat X-ray film (Rochester, N.Y.). The developed autoradiographs were than scanned for intensity using a video densitometer (Model 620, Biorad Corp., Richmond, Calif.).

7.2. RESULTS

Even in a normal disease free state, the expression of TCRs varies for the different subfamilies. Some subfamilies, e.g. Vβ8, Vβ6 and Vα10, are expressed quite frequently and the expression of others is fairly rare. For disease correlation, the increased levels of expression in disease are determined relative to these base levels.

Using cDNA synthesis, PCR amplification and slot blot hybridization procedures, paired RA samples including peripheral blood and synovial tissue derived T cell lines from each of 12 patients were analyzed relative to the expression in 5 normal peripheral blood controls. One basic assumption in this analysis is that the disease related T cells are more abundant at the site of the disease, e.g. the synovial membrane of patients with rheumatoid arthritis, than in the periphery.

An example of this analysis is shown in FIG. 6. The left panel of FIG. 6 shows the autoradiograph obtained when the T cell line ST-2 obtained from synovial tissue infiltrating lymphocytes was analyzed with the panel of Vβ TCR genes. The right side of this figure shows the densitometry trace. In this cell line, it is clear that several TCR Vβ genes (Vβ's 2, 4, 6, 7, 8, 11 and 18) are expressed with Vβ4 being expressed in highest amounts. To determine which of these correlate with disease, this pattern of expression was compared to the pattern of expression observed in the peripheral blood derived T cell lines (see FIGS. 7 and 8).

Figure 7:
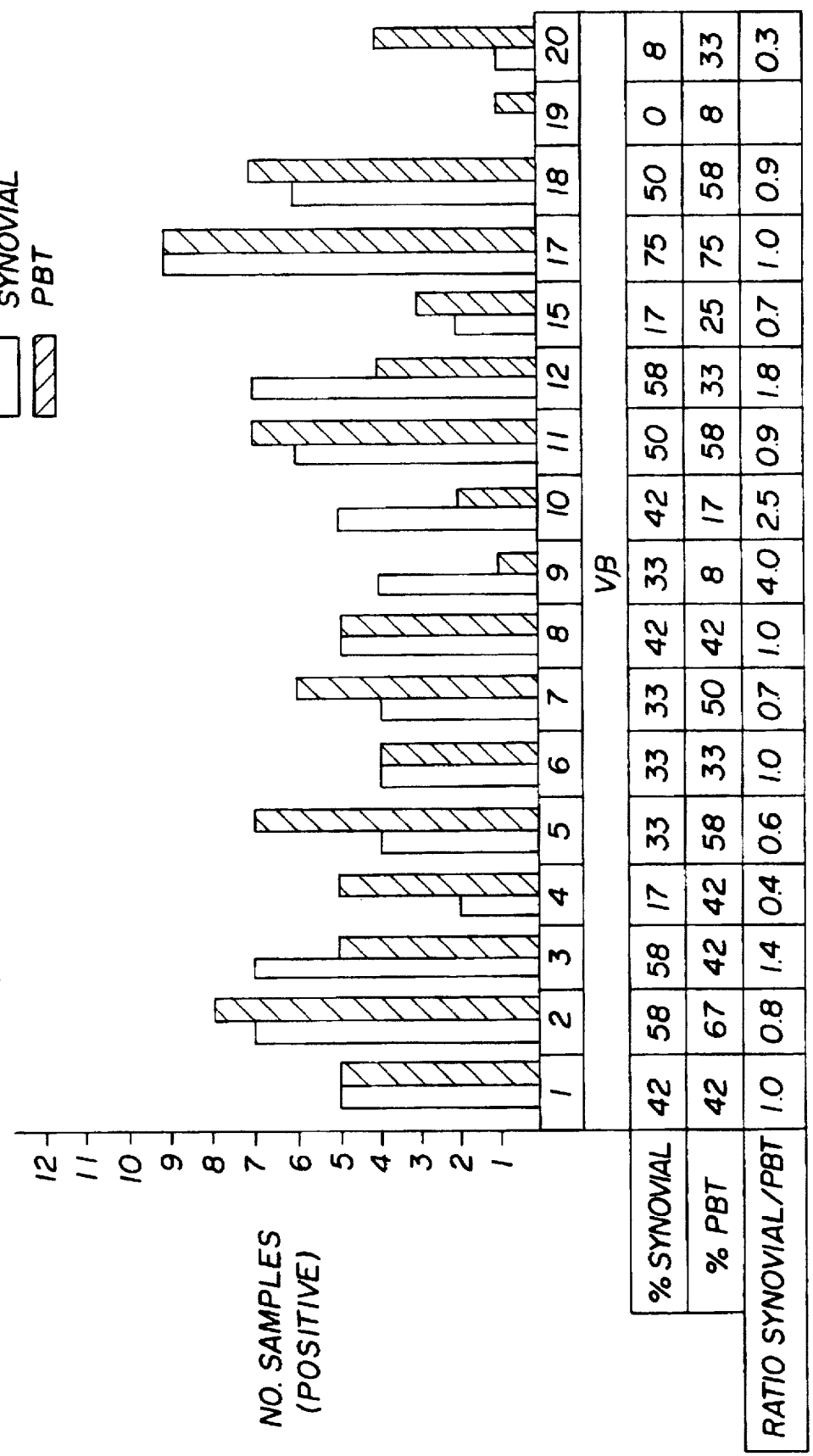
FIG. 7. Shows detection of Vβ gene usage in RA T cells. Shown are tabulated results of the expression of the panel of Vβ genes in 12 paired synovial tissue-derived and peripheral blood-derived T cell lines from RA patients. For the top part of the figure, the vertical axis represents the number of samples that were positive for a particular Vβ. The individual Vβ genes are indicated on the horizontal axis. Data derived from synovial T cells and peripheral blood T cells are plotted in pairs as open and crosshatched bars, respectively. For the bottom part of the figure, the frequencies of the individual Vβ genes in the 12 patient samples are shown (% synovial and % PBT). To indicate preferential usage of Vβ genes the synovial/peripheral blood ratio is shown.

FIG. 7 tabulates the results observed for Vβ gene expression in each of the paired synovium tissue and peripheral blood derived T cell lines from the 12 RA patients analyzed. The Y axis represents the number of patient samples (12 total) where a Vβ was observed by the densitometry analysis as illustrated in FIG. 6 for the ST-2 cell line. The X axis represents each of the 16 Vβ gene probes tested. Peripheral blood data is represented by a crosshatched bar and synovial tissue data is represented by an open bar for each Vβ. From this figure, it can be determined that in the 12 RA patient samples analyzed, Vβ3, Vβ9, Vβ10 and Vβ12 were expressed more often in the synovial tissue derived T cell lines than in the peripheral blood derived T cell lines. For example, the ratio of presence in synovium to presence in the peripheral blood sample was found to be 1.4 for Vβ3. By this analysis, the most frequently expressed Vβ genes in the synovium relative to the peripheral blood of rheumatoid arthritis patients were Vβ3, Vβ9, Vβ10 and Vβ12.

Figure 8:
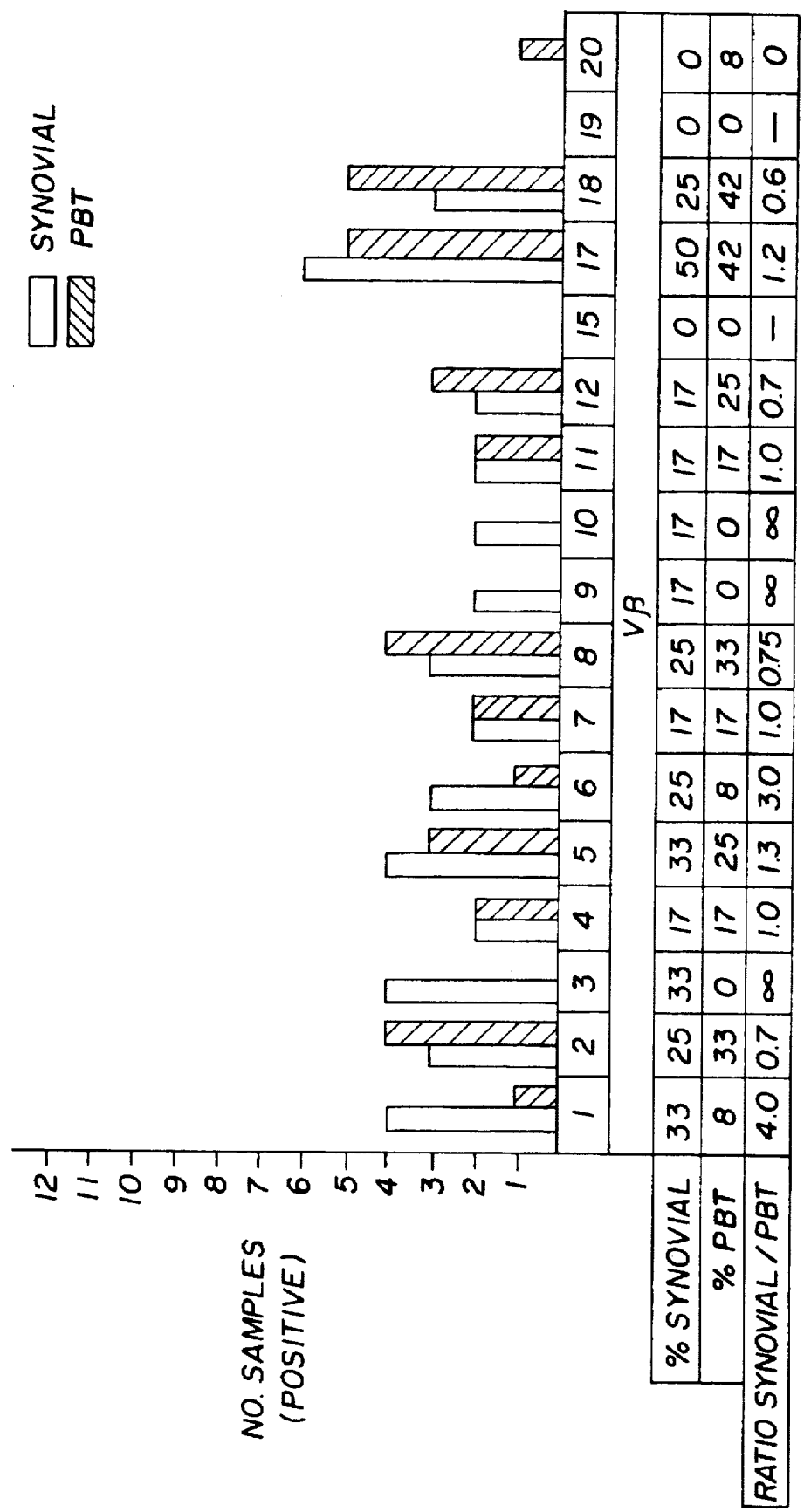
FIG. 8. Detection of dominant Vβ gene usage in RA T cells. This figure is similar to FIG. 7, except that the tabulated data includes only the expression of the most frequently occurring Vβ genes as determined by the densitometry trace. The most frequent or dominant Vβ was determined from the greatest peak height which was used as a standard. Any Vβ gene with a corresponding densitometry peak with height greater than 50% of the standard was used in the tabulation.

When the same data was analyzed as shown in FIG. 8, the frequently used genes were Vβ1 (ratio=4.0), Vβ3 (ratio=infinity), Vβ6 (ratio=3.0), Vβ9 (ratio=infinity), and Vβ10 (ratio=infinity). For the analysis in FIG. 8 only the dominant Vβ in each sample as determined by the densitometry trace was used, the assumption being that although the T cell line may contain varying subpopulations of T cells, the dominant subpopulation would be the most relevant one. The frequencies of Vβ3, Vβ9, and Vβ10 were high when the data from the 12 patients was analyzed either for total expression or dominant expression.

7.3. SUMMARY

This analysis has shown that T cell populations at the site of disease, e.g. the joint synovial membrane, appear to predominantly express specific Vβ chains. One mechanism of autoimmunity may be that disease-related autoantigens are recognized by the body's own T cells via specific T cell antigen receptor α, β, γ and δ chains. After antigen recognition, these T cells clonally expand to give rise to an oligoclonal population of disease-related T cells. Other mechanisms that may be involved include recruitment of specific cells to the disease site which would then represent an oligoclonal population of cells. In the total population of cells present at the disease site, the oligoclonal cells can be detected, as they will be using the TCR variable regions that are most frequently expressed. To date, our study has shown that the most frequently expressed Vβ genes in the synovial membrane of 12 RA patients were Vβ3, Vβ9, and Vβ10. To refine this correlation even more, patient HLA type, disease state and expression of TCR genes for α, β, γ and δ chains and for TCR Diversity-Joining region expression may be determined. It is expected that as patients are subgrouped by HLA type, the correlations of TCR gene usage and disease will become even stronger.

7.4. TREATMENT OF RHEUMATOID ARTHRITIS PATIENTS

WITH TCR α, β SPECIFIC REAGENTS

Once a disease correlation has been made between a disease state and specific TCR gene expression, then the next step is to develop TCR specific therapeutics. One class of such therapeutics are anti-TCR antibodies.

For the analysis presented supra on the preferential use of Vβ3.1 genes in rheumatoid arthritis patients, it is envisioned that a specific therapeutic could involve anti-TCR antibodies specific for Vβ3, in particular Vβ3.1. In a further embodiment, a multiple antibody cocktail of antibodies to Vβ3, in particular Vβ3.1, and Vβ9 or Vβ10, or both, can be used in a therapeutic. Such therapeutics would target only the T cell subsets expressing these Vβ TCRs and not effect other non-expressing T cells. Vβ3 specific antibodies have been produced as shown in Section 6, supra.

8. DEPOSIT OF HYBRIDOMAS

The following hybridoma cell lines, producing the indicated monoclonal antibody, have been deposited with the American Type Culture Collection, 12301 Parklawn Drive Rockville, Md., 20852, on Apr. 15, 1992 under the provisions of the Budapest Treaty on the International Recognition of the Deposit of Nueroorganisms for the Purposes of Patent Procedures, and have been assigned the listed accession numbers:

| Hybridoma | Monoclonal Antibody | Accession Number |
| --- | --- | --- |
| 5E4.AE | 5E4 | HB 11020 |
| 8F10.B2 | 8F10 | HB 11021 |

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof. The invention is not to be limited in scope by the microorganisms deposited or the specific embodiments described herein, since such embodiments are intended as but single illustrations of one aspect of the invention, and microorganisms that are functionally equivalent are within the scope of the invention. It will be understood that the invention is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A monoclonal antibody or antigen binding fragment thereof which is reactive with the same epitope as monoclonal antibody 5E4 produced by the hybridoma deposited with the ATCC and assigned accession number HB11020.

2. A monoclonal antibody or antigen binding fragment thereof which is reactive with the same epitope as monoclonal antibody 8F10 produced by the hybridoma deposited with the ATCC and assigned accession number HB11021.

3. A monoclonal antibody or antigen binding fragment thereof reactive with an epitope of a Vβ3.1 variable region of a T cell receptor, said antibody designated 5E4 and produced by the hybridoma deposited with the ATCC and assigned accession number HB11020.

4. A monoclonal antibody or antigen binding fragment thereof reactive with an epitope of a Vβ3.1 variable region of a T cell receptor, said antibody designated 8F10 and produced by the hybridoma deposited with the ATCC and assigned accession number HB11021.

5. An antigen binding fragment of the monoclonal antibody of claim 3, wherein said fragment is selected from the group consisting of a Fv fragment, a Fab fragment, a Fab' fragment, and a F(ab')$_2$ fragment.

6. An antigen binding fragment of the monoclonal antibody of claim 4, wherein said fragment is selected from the group consisting of a Fv fragment, a Fab fragment, a Fab' fragment, and a F(ab')$_2$ fragment.

7. A hybridoma cell line, which produces the monoclonal antibody of claim 1 or claim 2.

8. A hybridoma cell line, which produces the monoclonal antibody of claim 3, deposited with the ATCC and assigned accession number HB 11020.

9. A hybridoma cell line, which produces the monoclonal antibody of claim 4, deposited with the ATCC and assigned accession number HB 11021.

10. A monoclonal antibody or antigen binding fragment thereof reactive with the same epitope of a Vβ3.1 variable region of a T cell antigen receptor as recognized by the monoclonal antibody or antigen binding fragment thereof of any one of claims 1, 2, 3, and 4 produced by the process comprising:

(a) preparing a purified, soluble, recombinant Vβ3.1 T cell antigen receptor polypeptide;

(b) immunizing a mouse, rat or rabbit with said purified, soluble, recombinant Vβ3.1 T cell antigen receptor polypeptide;

(c) boosting said mouse, rat, or rabbit at least one time by re-immunizing with said purified, soluble, recombinant Vβ3.1 T cell antigen receptor polypeptide;

(d) prescreening said re-immunized mouse, rat or rabbit of step(c) at least once after said re-immunization using said purified, soluble, recombinant Vβ3.1 T cell antigen receptor polypeptide to detect antibody production in said mouse, rat or rabbit of antibodies, wherein said antibodies of step (d) are reactive with said polypeptide;

(e) isolating antibody producing cells from said mouse, rat, or rabbit;

(f) fusing said antibody producing cells with an immortal cell line to produce an immortal antibody-secreting cell line;

(g) screening said immortal antibody-secreting cell line for production of antibodies reactive with Vβ3.1 using said purified, soluble, recombinant Vβ3.1 T cell antigen receptor polypeptide;

(h) further screening said immortal antibody-secreting cell line for the production of antibodies reactive with Vβ3.1 by measuring the ability of antibodies produced by the cell line to immunoprecipitate cell surface-expressed Vβ3.1 T cell antigen protein;

(i) further screening said immortal antibody-secreting cell line for the production of antibodies reactive with Vβ3.1 by incubating Vβ3.1 T cells with supernatant of a culture of said immortal antibody secreting cell line and measuring T cell proliferation; and (j) isolating antibodies testing positive in the screening procedures (g), (h), and (i).

11. A derivative of the monoclonal antibody which is reactive with an epitope of a Vβ3.1 variable region of a T cell receptor and is produced by the hybridoma deposited with the ATCC and assigned accession number HB11020 or HB11021 selected from the group consisting of:

(a) a mouse-human chimeric antibody, wherein the light and heavy chain variable regions are derived from the murine monoclonal antibody produced by the hybridoma HB11020 or HB11021 and the constant region is derived from a human antibody;

(b) a humanized antibody wherein hypervariable regions are derived from the murine monoclonal antibody produced by the hybridoma HB11020 or HB11021 and other regions derived from a human antibody;

(c) an immunoconjugate wherein the monoclonal antibody produced by the hybridoma HB11020 or HB11021 or antigen binding fragment thereof is conjugated to a detectable label;

(d) an immunoconjugate wherein the monoclonal antibody produced by the hybridoma HB11020 or HB11021 or antigen binding fragment thereof is conjugated to a therapeutically useful molecule; and
(e) a single chain antibody wherein fragments of the heavy and light chain comprising at least the hypervariable regions of the monoclonal antibody produced by the hybridoma HB11020 or HB11021 are linked to form a single-chain polypeptide capable of binding to a Vβ3.1 T cell antigen receptor.

* * * * *

SEQUENCE LISTING ( 1 ) GENERAL INFORMATION:

( i i i ) NUMBER OF SEQUENCES:8

( 2 ) INFORMATION FOR SEQ ID NO: 1:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:DNA ( x i ) SEQUENCE DESCRIPTION: SEQ ID NO: 1:

GGA GAT ATT CCT GAG GGG TAC        21

( 2 ) INFORMATION FOR SEQ ID NO: 2:

( i ) SEQUENCE CHARACTERISTICS:

( A ) LENGTH:21 base pairs
           ( B ) TYPE:nucleic acid
           ( C ) STRANDEDNESS:single
           ( D ) TOPOLOGY:linear ( i i ) MOLECULE TYPE:DNA ( x i ) SEQUENCE DESCRIPTION: SEQ ID NO: 2:

GAT GTG AAA GTA ACC CAG AGC                                                          21

( 2 ) INFORMATION FOR SEQ ID NO: 3:

( i ) SEQUENCE CHARACTERISTICS:
           ( A ) LENGTH:26 base pairs
           ( B ) TYPE:nucleic acid
           ( C ) STRANDEDNESS:single
           ( D ) TOPOLOGY:linear ( i i ) MOLECULE TYPE:DNA ( x i ) SEQUENCE DESCRIPTION: SEQ ID NO: 3:

CTG ATG GCT CAA ACA CAG CGA CCT CG                                                   26

( 2 ) INFORMATION FOR SEQ ID NO: 4:

( i ) SEQUENCE CHARACTERISTICS:
           ( A ) LENGTH:30 base pairs
           ( B ) TYPE:nucleic acid
           ( C ) STRANDEDNESS:single
           ( D ) TOPOLOGY:linear ( i i ) MOLECULE TYPE:DNA ( x i ) SEQUENCE DESCRIPTION: SEQ ID NO: 4:

CCT GGG GTA GAG CAG ACT GTT CGT AGC ATG                                              30

( 2 ) INFORMATION FOR SEQ ID NO: 5:

( i ) SEQUENCE CHARACTERISTICS:
           ( A ) LENGTH:26 base pairs
           ( B ) TYPE:nucleic acid
           ( C ) STRANDEDNESS:single
           ( D ) TOPOLOGY:linear ( i i ) MOLECULE TYPE:DNA ( x i ) SEQUENCE DESCRIPTION: SEQ ID NO: 5:

CTA CGA ACA GTC TGC TCT ACC CCA GG                                                   26

( 2 ) INFORMATION FOR SEQ ID NO: 6:

( i ) SEQUENCE CHARACTERISTICS:
           ( A ) LENGTH:29 base pairs
           ( B ) TYPE:nucleic acid
           ( C ) STRANDEDNESS:single
           ( D ) TOPOLOGY:linear ( i i ) MOLECULE TYPE:DNA ( x i ) SEQUENCE DESCRIPTION: SEQ ID NO: 6:

GCA TAC AGA TGC TAA AGT AAC CCA GAG AG                                               29

( 2 ) INFORMATION FOR SEQ ID NO: 7:

( i ) SEQUENCE CHARACTERISTICS:
           ( A ) LENGTH:18 base pairs
           ( B ) TYPE:nucleic acid
           ( C ) STRANDEDNESS:single
           ( D ) TOPOLOGY:linear

```
        (  i  i  ) MOLECULE TYPE:DNA (  x  i  ) SEQUENCE DESCRIPTION: SEQ ID NO: 7:

TTA GAG TCT CTC AGC TGG                                                        18

( 2 ) INFORMATION FOR SEQ ID NO: 8:

(  i  ) SEQUENCE CHARACTERISTICS:
                ( A ) LENGTH:18 base pairs
                ( B ) TYPE:nucleic acid
                ( C ) STRANDEDNESS:single
                ( D ) TOPOLOGY:linear (  i  i  ) MOLECULE TYPE:DNA (  x  i  ) SEQUENCE DESCRIPTION: SEQ ID NO: 8:

TTC TGA TGG CTC AAA CAC                                                        18
```